US010544471B2

(12) United States Patent
Dotson et al.

(10) Patent No.: US 10,544,471 B2
(45) Date of Patent: *Jan. 28, 2020

(54) METHODS FOR SEQUENCE-DIRECTED MOLECULAR BREEDING

(71) Applicant: Monsanto Technology LLC, St. Louis, MO (US)

(72) Inventors: Stanton B. Dotson, Chesterfield, MO (US); Fenggao Dong, Chesterfield, MO (US); Frederic Achard, Kirkwood, MO (US); Sam Eathington, St. Louis, MO (US); Nengbing Tao, O'Fallon, MO (US); Zoe McKiness, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 115 days.

This patent is subject to a terminal disclaimer.

(21) Appl. No.: 15/707,615

(22) Filed: Sep. 18, 2017

(65) Prior Publication Data

US 2018/0004894 A1    Jan. 4, 2018

Related U.S. Application Data

(63) Continuation of application No. 14/856,733, filed on Sep. 17, 2015, which is a continuation of application No. 13/247,528, filed on Sep. 28, 2011, which is a continuation of application No. 12/135,564, filed on Jun. 9, 2008, now abandoned.

(60) Provisional application No. 60/942,707, filed on Jun. 8, 2007.

(51) Int. Cl.
| | |
|---|---|
| *A01H 1/04* | (2006.01) |
| *C12Q 1/6827* | (2018.01) |
| *C12Q 1/6874* | (2018.01) |
| *C12Q 1/6895* | (2018.01) |
| *G16B 30/00* | (2019.01) |
| *G16B 35/00* | (2019.01) |
| *G16C 20/60* | (2019.01) |

(52) U.S. Cl.
CPC ............ *C12Q 1/6895* (2013.01); *A01H 1/04* (2013.01); *C12Q 1/6827* (2013.01); *C12Q 1/6874* (2013.01); *G16B 30/00* (2019.02); *G16B 35/00* (2019.02); *G16C 20/60* (2019.02); *C12Q 2600/13* (2013.01); *C12Q 2600/156* (2013.01)

(58) Field of Classification Search
CPC ....................... C12Q 1/6827; C12Q 1/6895
See application file for complete search history.

(56) References Cited

U.S. PATENT DOCUMENTS

| | | | |
|---|---|---|---|
| 4,757,011 A | 7/1988 | Chaleff et al. | |
| 4,769,061 A | 9/1988 | Comai | |
| 4,940,835 A | 7/1990 | Shah et al. | |
| 4,971,908 A | 11/1990 | Kishore et al. | |
| 5,015,580 A | 5/1991 | Christou et al. | |
| 5,384,253 A | 1/1995 | Krzyzek et al. | |
| 5,437,697 A | 8/1995 | Sebastian et al. | |
| 5,492,547 A | 2/1996 | Johnson | |
| 5,508,184 A | 4/1996 | Negrutiu et al. | |
| 5,538,880 A | 7/1996 | Lundquist et al. | |
| 5,550,318 A | 8/1996 | Adams et al. | |
| 5,591,616 A | 1/1997 | Hiei et al. | |
| 5,635,055 A | 6/1997 | Sweet et al. | |
| 5,824,877 A | 10/1998 | Hinchee et al. | |
| 5,846,719 A * | 12/1998 | Brenner | B01J 19/0046 506/3 |
| 5,981,832 A | 11/1999 | Johnson | |
| 5,981,840 A | 11/1999 | Zhao et al. | |
| 6,160,208 A | 12/2000 | Lundquist et al. | |
| 6,207,367 B1 | 3/2001 | Helentjaris et al. | |
| 6,219,964 B1 | 4/2001 | Byrum et al. | |
| 6,384,301 B1 | 5/2002 | Martinell et al. | |
| 6,399,855 B1 | 6/2002 | Beavis | |
| 6,399,861 B1 | 6/2002 | Anderson et al. | |
| 6,403,865 B1 | 6/2002 | Koziel et al. | |
| 6,455,758 B1 | 9/2002 | Johnson | |
| 7,157,564 B1 * | 1/2007 | Mittmann | C12Q 1/6837 536/23.1 |
| 7,485,425 B2 * | 2/2009 | Spier | C12Q 1/6858 435/6.12 |
| 7,703,238 B2 | 4/2010 | Depperman et al. | |
| 8,603,749 B2 * | 12/2013 | Gillevet | C12Q 1/6858 435/6.12 |
| 2005/0015827 A1 | 1/2005 | Podlich et al. | |
| 2005/0216545 A1 | 2/2005 | Aldrich et al. | |
| 2005/0071901 A1 | 3/2005 | Sebastian | |

(Continued)

FOREIGN PATENT DOCUMENTS

| | | |
|---|---|---|
| EP | 0 534 858 A1 | 3/1993 |
| EP | 1 724 348 A2 | 11/2006 |

(Continued)

OTHER PUBLICATIONS

Collard et al (Euphytica (2005) 142: 169-196) (Year: 2005).*
Mohan et al (Molecular Breeding 3 (1997) 87-103) (Year: 1997).*
Binladen eta al (PLOS ONE 2(2): e197. Published: Feb. 14, 2007) (Year: 2007).*
Berke et al., "Quantitative Trait Loci for Flowering, Plant and Ear Height, and Kernel Traits in Maize," *Crop Sci.*, 35:1542-1549 (1995).

(Continued)

*Primary Examiner* — Lee A Visone
(74) *Attorney, Agent, or Firm* — James E. Davis; Arnold & Porter Kaye Scholer LLP

(57) ABSTRACT

The present invention provides breeding methods and compositions to enhance the germplasm of a plant by the use of direct nucleic acid sequence information. The methods describe the identification and accumulation of preferred nucleic acid sequences in the germplasm of a breeding population of plants.

10 Claims, 13 Drawing Sheets

Specification includes a Sequence Listing.

(56) References Cited

U.S. PATENT DOCUMENTS

| | | | |
|---|---|---|---|
| 2005/0204780 | A1 | 9/2005 | Moridaira et al. |
| 2005/0213435 | A1 | 9/2005 | Bakos et al. |
| 2005/0218305 | A1 | 10/2005 | Tsukamoto et al. |
| 2006/0042527 | A1 | 3/2006 | Deppermann |
| 2006/0046264 | A1 | 3/2006 | Deppermann |
| 2006/0048247 | A1 | 3/2006 | Deppermann |
| 2006/0048248 | A1 | 3/2006 | Deppermann |
| 2006/0107348 | A1 | 5/2006 | Wu et al. |
| 2006/0200878 | A1 | 9/2006 | Lutfiyya et al. |
| 2006/0282911 | A1 | 12/2006 | Bull et al. |
| 2007/0011775 | A1 | 1/2007 | Allen et al. |
| 2007/0054288 | A1 | 3/2007 | Su et al. |
| 2007/0204366 | A1 | 8/2007 | Deppermann et al. |
| 2007/0207485 | A1 | 9/2007 | Deppermann et al. |
| 2008/0083042 | A1 | 4/2008 | Butruille et al. |
| 2013/0123113 | A1* | 5/2013 | Tao .................... A01H 1/04 506/2 |
| 2016/0098515 | A1* | 4/2016 | Dotson .................. A01H 1/04 506/8 |

FOREIGN PATENT DOCUMENTS

| | | |
|---|---|---|
| EP | 2 511 381 B1 | 1/2017 |
| WO | WO 90/04651 A1 | 5/1990 |
| WO | WO 01/49104 A2 | 7/2001 |
| WO | WO 03/052101 A1 | 6/2003 |
| WO | WO 2005/000006 A2 | 1/2005 |
| WO | WO 2006/137733 A1 | 12/2006 |
| WO | WO 2006/137734 A1 | 12/2006 |
| WO | WO 2007/057402 A1 | 5/2007 |
| WO | WO 2007/103786 A2 | 9/2007 |
| WO | WO 2008/021413 A1 | 2/2008 |

OTHER PUBLICATIONS

Communication Pursuant to Article 94(3) EPC dated Jun. 2, 2014, in European Patent Application No. 11180635.2.
Communication Pursuant to Article 94(3) EPC dated Feb. 16, 2015, in European Patent Application No. 11180635.2.
Communication Pursuant to Article 94(3) EPC dated Dec. 15, 2015, in European Patent Application No. 11180635.2.
Communication Under Rule 71(3) EPC—Intention to Grant—dated Aug. 16, 2016, in European Patent Application No. 11180635.2.
Communication Pursuant to Rule 69 EPC dated Oct. 22, 2012, in European Patent Application No. 11180635.2.
Decision to Grant a European Patent Pursuant to Article 97(1) EPC, dated Jan. 5, 2017, in European Patent Application No. 11180635.2.
Dellaporta et al., "A Plant DNA Minipreparation: Version II," *Plant Molecular Biology Reporter*, 1(4):19-21 (1983).
Doebley et al., "The Molecular Genetics of Crop Domestication," *Cell*, 127(7):1309-1321 (2006).
Extended European Search Report dated Sep. 17, 2012, in European Patent Application No. 11180635.2.
Flint-Garcia et al., "Structure of Linkage Disequilibrium in Plants," *Annual Review of Plant Biology*, 54:357-374 (2003).
International Search Report dated Jul. 8, 2009, in International Patent Application No. PCT/US2008/066263.
Invitation to Remedy Deficiencies Pursuant to Rule 30(3) EPC / Rule 163(3) EPC dated May 15, 2012, in European Patent Application No. 11180635.2.
Nordborg et al., "Linkage disequilibrium: what history has to tell us," *TRENDS in Genetics*, 18(2):83-90 (2002).
Phogat et al., "A four-element based transposon system for allele specific tagging in plants—theoretical considerations," *Journal of Biosciences*, 25(1):57-63 (2000).
Response to Communication Pursuant to Rule 69 EPC dated Oct. 22, 2012, as filed on Apr. 17, 2013, in European Patent Application No. 11180635.2.
Response to Communication Pursuant to Article 94(3) EPC dated Jun. 2, 2014, as filed on Dec. 3, 2014, in European Patent Application No. 11180635.2.
Response to Communication Pursuant to Article 94(3) EPC dated Feb. 16, 2015, as filed on Aug. 19, 2015, in European Patent Application No. 11180635.2.
Response to Communication Pursuant to Article 94(3) EPC dated Dec. 15, 2015, as filed on Apr. 6, 2016, in European Patent Application No. 11180635.2.
Response to Invitation to Remedy Deficiencies Pursuant to Rule 30(3) EPC / Rule 163(3) EPC dated May 15, 2012, as filed on Jul. 10, 2012, in European Patent Application No. 11180635.2.
Service et al., "Gene Sequencing. The Race for the $1000 Genome," *Science*, 311:1544-1546 (2006).
Somers et al., "Molecular Breeding for Multiple Pest Resistance in Wheat," *Developments in Plant Breeding*, 667-676 (2007).
Tong et al, "Identification of HDAC10, a novel class II human histone deacetylase containing a leucine-rich domain," *Nucleic Acids Research*, 30(5):1114-1123(2002).
Tong et al., "Single nucleotide polymorphism detection by combinatorial fluorescence energy transfer tags and biotinylated dideoxynucleotides," *Nucleic Acids Res.*, 30(5): e19 (2002).
Xu et al., "Marker-Assisted Selection in Plant Breeding: From Publications to Practice," *Crop Science*, 48(2):391-407 (2008).
Yamasaki et al., "A Large-Scale Screen for Artificial Selection in Maize Identifies Candidate Agronomic Loci for Domestication and Crop Improvement," *The Plant Cell*, 17:2859-2872 (2005).
Zhang et al., "Quantifying DNA-protein binding specificities by using oligonucleotide mass tags and mass spectroscopy," *PNAS*, 104(9):3061-3066 (2007).
Berry et al., "Barcoded Primers Used in Multiplex Amplicon Pyrosequencing Bias Amplification," *Applied and Environmental Microbiology*, 77(21):7846-7849 (2011).
Donini et al., "The Potential of Microsatellites for High Throughput Genetic Diversity Assessment in Wheat and Barley," *Genetic Resources and Crop Evolution*, 45:415-421 (1998).
Hoffman et al., "DNA Bar Coding and Pyrosequencing to Identify Rare HIV Drug Resistance Mutations," Nucleic Acids Research 35(13):1-8 (2007).

* cited by examiner

SEQUENCE LISTING

<160> NUMBER OF SEQ ID NOS: 14

<210> SEQ ID NO 1
<211> LENGTH: 33
<212> TYPE: DNA
<213> ORGANISM: Glycine max

<400> SEQUENCE: 1
acactctttc cctacacgac gctcttccga tct                33

<210> SEQ ID NO 2
<211> LENGTH: 20
<212> TYPE: DNA
<213> ORGANISM: Glycine max

<400> SEQUENCE: 2
cattggcacc catgttatcc                               20

<210> SEQ ID NO 3
<211> LENGTH: 34
<212> TYPE: DNA
<213> ORGANISM: Glycine max

<400> SEQUENCE: 3
caagcagaag acggcatacg agctcttccg atct               34

<210> SEQ ID NO 4
<211> LENGTH: 26
<212> TYPE: DNA
<213> ORGANISM: Glycine max

<400> SEQUENCE: 4
gacttagatc acataggcag acatac                        26

<210> SEQ ID NO 5
<211> LENGTH: 33
<212> TYPE: DNA
<213> ORGANISM: Glycine max

<400> SEQUENCE: 5
acactctttc cctacacgac gctcttccga tct                33

<210> SEQ ID NO 6
<211> LENGTH: 21
<212> TYPE: DNA
<213> ORGANISM: Glycine max

<400> SEQUENCE: 6
taagtgacac tggagatgtg g                                          21

<210> SEQ ID NO 7
<211> LENGTH: 33
<212> TYPE: DNA
<213> ORGANISM: Glycine max

<400> SEQUENCE: 7
acactctttc cctacacgac gctcttccga tct                             33

<210> SEQ ID NO 8
<211> LENGTH: 26
<212> TYPE: DNA
<213> ORGANISM: Glycine max

<400> SEQUENCE: 8
cagaaagtat tggtaaagta ctggta                                     26

<210> SEQ ID NO 9
<211> LENGTH: 34
<212> TYPE: DNA
<213> ORGANISM: Glycine max

<400> SEQUENCE: 9
caagcagaag acggcatacg agctcttccg atct                            34

<210> SEQ ID NO 10
<211> LENGTH: 24
<212> TYPE: DNA
<213> ORGANISM: Glycine max

<400> SEQUENCE: 10
taaatattcc attgaggccc acta                                       24

<210> SEQ ID NO 11
<211> LENGTH: 16
<212> TYPE: DNA
<213> ORGANISM: Glycine max

<400> SEQUENCE: 11
gtctgcctat agtgag                                                16

<210> SEQ ID NO 12
<211> LENGTH: 33
<212> TYPE: DNA
<213> ORGANISM: Glycine max

<400> SEQUENCE: 12
acactctttc cctacacgac gctcttccga tct                             33

<210> SEQ ID NO 13
<211> LENGTH: 34
<212> TYPE: DNA
<213> ORGANISM: Glycine max

<400> SEQUENCE: 13
caagcagaag acggcatacg agctcttccg atct                            34

<210> SEQ ID NO 14
<211> LENGTH: 16

```
<212> TYPE: DNA
<213> ORGANISM: Glycine max

<400> SEQUENCE: 14
ctcactatag gcagac                                                  16
```

METHODS FOR SEQUENCE-DIRECTED MOLECULAR BREEDING

CROSS REFERENCE TO RELATED APPLICATIONS

This application is a continuation of U.S. patent application Ser. No. 14/856,733 (filed Sep. 17, 2015), which is a continuation of U.S. patent application Ser. No. 13/247,528 (filed Sep. 28, 2011), which claims priority to U.S. patent application Ser. No. 12/135,564 (filed Jun. 9, 2008), now abandoned, which claims priority from U.S. Provisional Application No. 60/942,707 (filed Jun. 8, 2007). The entire texts of U.S. patent application Ser. No. 13/247,528, U.S. patent application Ser. No. 12/135,564 and U.S. Provisional Application Ser. No. 60/942,707 are hereby incorporated by reference herein.

FIELD OF INVENTION

This invention is in the field of plant breeding. More specifically, this invention relates to the use of high throughput sequencing technology in activities related to germplasm improvement.

BACKGROUND OF INVENTION

The primary objectives of plant breeding are to select an optimal pair of parents to make a cross and then to select one or more superior progeny resulting from that cross. In hybrid crops, a third objective is to identify a tester to make up high performing hybrid seed. Traditional plant breeding has relied on visual observations and performance data on the plants or lines in order to make selections to meet one of the aforementioned objectives.

In recent years, molecular breeding has demonstrated promise for improving the breeding process and enhancing the rate of genetic gain. In molecular breeding, molecular markers provide a basis for parental, progeny or tester selections; this process may be used in conjunction with phenotype-based selection as well. Inclusion of genetic markers in breeding programs has accelerated the identification and accumulation of valuable traits into germplasm pools compared to that achieved based only on phenotypic data. Herein, "germplasm" includes breeding germplasm, breeding populations, collection of elite inbred lines, populations of random mating individuals, and biparental crosses.

For molecular breeding to be effective, the differences in marker genotypes must be heritably associated to one or more phenotypic or performance traits. These associations are established by correlating the marker genotypes to lines or populations segregating for one or more traits. Genetic marker alleles (an "allele" is an alternative sequence at a locus) are used to identify plants that contain a desired genotype at one or more loci, and that are expected to transfer the desired genotype, along with a desired phenotype for one or more traits, to their progeny. Markers that are highly correlated with a phenotype are assumed to be genetically linked to the trait, thus the marker can then be used as a basis for selection decisions in lieu of evaluating the trait per se. Markers that are not correlated will be inherited independently of the trait and are not useful for selections, but can be valuable in comparing similarities and/or measuring genetic distances among varieties and lines. Ideally, the marker will represent the actual genomic variation responsible for a trait and will therefore always segregate with the trait, although the correlations can be masked by phenomena such as environmental interactions or epistatic effects.

Initial marker platforms for molecular breeding did not require a priori knowledge of underlying sequence. These markers were based on restriction fragment length polymorphisms (RFLPs). Random or directed DNA probes were used in Southern hybridization protocols to identify target fragments whose size varied depending on the location and distance between a pair of restriction enzyme recognition sites. These differences in size could be correlated to traits in test populations. The DNA probes were then used as markers that could detect the underlying restriction fragment length polymorphisms and in turn be used to predict a correlated trait. Other types of markers have been used that require a priori knowledge of the underlying sequence and include but are not limited to fingerprinting using amplified fragment length polymorphisms (AFLPs) or universal PCR primers (i.e. RICE primers).

In recent years, markers have been developed based on the knowledge of an underlying sequence. For example, microsatellite or simple sequence repeat (SSR) markers rely on PCR and gel electrophoresis to elucidate variation in the length of DNA repeat sequences. The differences in repeat length, as revealed by the markers, can correlate to associated traits if the target repeat is genetically linked to the trait.

However, traditional marker platforms are suboptimal because they are not suited for automation or high throughput techniques. In addition, traditional marker platforms are susceptible to false marker-trait associations wherein the identity of a genotype between two lines may not reflect a common parent but a convergent sequence, which is problematic for tracking specific marker alleles across multiple generations.

Other types of variations useful as traditional markers are single nucleotide polymorphisms (SNPs). These are single base changes which differ between two lines and will segregate with a trait in which they are genetically linked. SNPs can be detected by a variety of commercially available marker technologies. Markers based on SNPs have gained in popularity due to the ease and accuracy of detection, compatibility with information systems and low cost. However, SNP markers are still an indirect tool for querying underlying sequence and a SNP marker is restricted to only detecting two alleles, not the four possible nucleotides that might be found at any given nucleotide position.

Thus, there is a need in the art for methods to quickly and accurately determine direct sequence information from at least one plant genome for the purpose of facilitating plant breeding activities such as line development, germplasm diversity analyses, rare allele mining, purity testing, quality assurance, introgression of specific genomic regions, stacking of genomic regions, prediction of line performance, and prediction of hybrid performance.

SUMMARY

This invention describes novel methods that utilize high throughput sequencing and molecular breeding methodologies to enable the use of direct sequencing information in molecular plant breeding. The invention also includes means to selectively target specific loci and to DNA tag samples prior to sequence determination. Taken together, the methods of the invention enable plant breeders better tools for parent selection, progeny selection, choosing tester combinations, developing pedigrees, fingerprinting samples, screening for haplotype diversity, ensuring quality, assessing germplasm diversity, measure breeding progress, providing variety or line descriptions and for building databases of sequence associations to trait and performance data. Such databases provide the basis for calculating nucleic acid effect estimates for one or more traits, wherein associations can be made de novo or by leveraging historical nucleic acid sequence-trait association data.

The present invention provides methods for Sequence Directed Selection (SDS), Sequence Directed Breeding (SDB) and Sequence Directed Fingerprinting (SDF) and its novel application for making parent selections, progeny selections, tester combinations, introgression of allelic variants and directed selection of at least one variant between at least two germplasm entries, fingerprints, pedigrees and for building databases of haplotype and phenotype information which can be used to calculate nucleic acid sequence effect estimates and, ultimately, breeding values. This a priori information facilitates decision making for Sequence Directed Predictive Breeding (SDPB).

In the present invention, breeding selections are conducted directly on a sequence, rather than indirectly on a marker, basis, wherein a first plant is crossed with a second plant that contains at least one sequence that is different from the first plant sequence or sequences; and at least one progeny plant is selected by detecting the sequence or set of sequences of the first plant, wherein the progeny plant comprises in its genome one or more sequences of interest of the first plant and at least one sequence of interest of the second plant; and the progeny plant is used in activities related to germplasm improvement, herein defined as including using the plant for line and variety development, hybrid development, transgenic event selection, making breeding crosses, testing and advancing a plant through self fertilization, purification of lines or sublines, using plant or parts thereof for transformation, using plants or parts thereof for candidates for expression constructs, and using plant or parts thereof for mutagenesis.

The present invention includes a method for breeding of a plant, such as maize (*Zea mays*), soybean (*Glycine max*), cotton (*Gossypium hirsutum*), peanut (*Arachis hypogaea*), barley (*Hordeum vulgare*); oats (*Avena sativa*); orchard grass (*Dactylis glomerata*); rice (*Oryza sativa*, including indica and japonica varieties); *sorghum* (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*), members of the genus *Brassica*, broccoli, cabbage, carrot, cauliflower, Chinese cabbage, cucumber, dry bean, eggplant, fennel, garden beans, gourd, leek, lettuce, melon, okra, onion, pea, pepper, pumpkin, radish, spinach, squash, sweet corn, tomato, watermelon, ornamental plants, and other fruit, vegetable, tuber, oilseed, and root crops, wherein oilseed crops include soybean, canola, oil seed rape, oil palm, sunflower, olive, corn, cottonseed, peanut, flaxseed, safflower, and coconut, with enhanced traits comprising at least one sequence of interest, further defined as conferring a preferred property selected from the group consisting of herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, other agronomic traits, traits for industrial uses, or traits for improved consumer appeal, wherein said traits may be nontransgenic or transgenic.

In one embodiment, the invention is directed to a method of plant breeding. The method comprises determining the sequence of a plurality of nucleic acids within the genome of at least one or more plants in a breeding population; associating each of the nucleic acid sequences with a numerical value wherein the numerical value is related to one or more phenotypic traits; and making a plant breeding decision for the one or more plants based on the association.

In another embodiment, the invention is directed to a method of plant breeding. The method comprises providing a breeding population comprising one or more plants wherein at least one nucleic acid is sequenced for at least one locus for each plant in the population; utilizing historical marker-phenotypic trait associations to determine a nucleic acid sequence effect estimate for a nucleic acid sequence at a locus; and ranking nucleic acid sequences based on the determined nucleic acid sequence effect estimate for any given phenotypic trait. The ranking is then used to make plant breeding decisions.

In another embodiment, the invention is directed to a method of plant breeding. The method comprises establishing a fingerprint map defining a plurality of loci within the genome of a breeding population; associating a QTL allele with known map location with a phenotypic trait in a mapping population; and assaying for presence of the QTL allele and at least one nucleic acid sequence within the plurality of loci to predict expression of the phenotypic trait in a population other than the mapping population.

In another embodiment, the invention is directed to a method of marker assisted breeding. The method comprises providing a breeding population comprising at least two plants and associating at least one phenotypic trait with a locus of the genome of the plants, provided that the locus is defined by at least one nucleic acid sequence. The population is then assayed for the presence of at least one nucleic acid sequence of the locus to predict the expression of at least one phenotypic trait in a progeny plant of the breeding population.

In another embodiment, the invention is directed to a method of selecting a breeding population for use in a breeding program. The method comprises providing at least two distinct breeding populations; establishing a database of breeding values for at least two loci of up to 10 centimorgans for each breeding population; ranking the breeding values of the alleles for each breeding population; and selecting a breeding population with a higher composite breeding value.

Further areas of applicability will be more particularly described below in relation to the detailed description. It should be understood that the description and specific examples are intended for purposes of illustration only and are not intended to limit the scope of the present disclosure.

DETAILED DESCRIPTION

Figure 1:
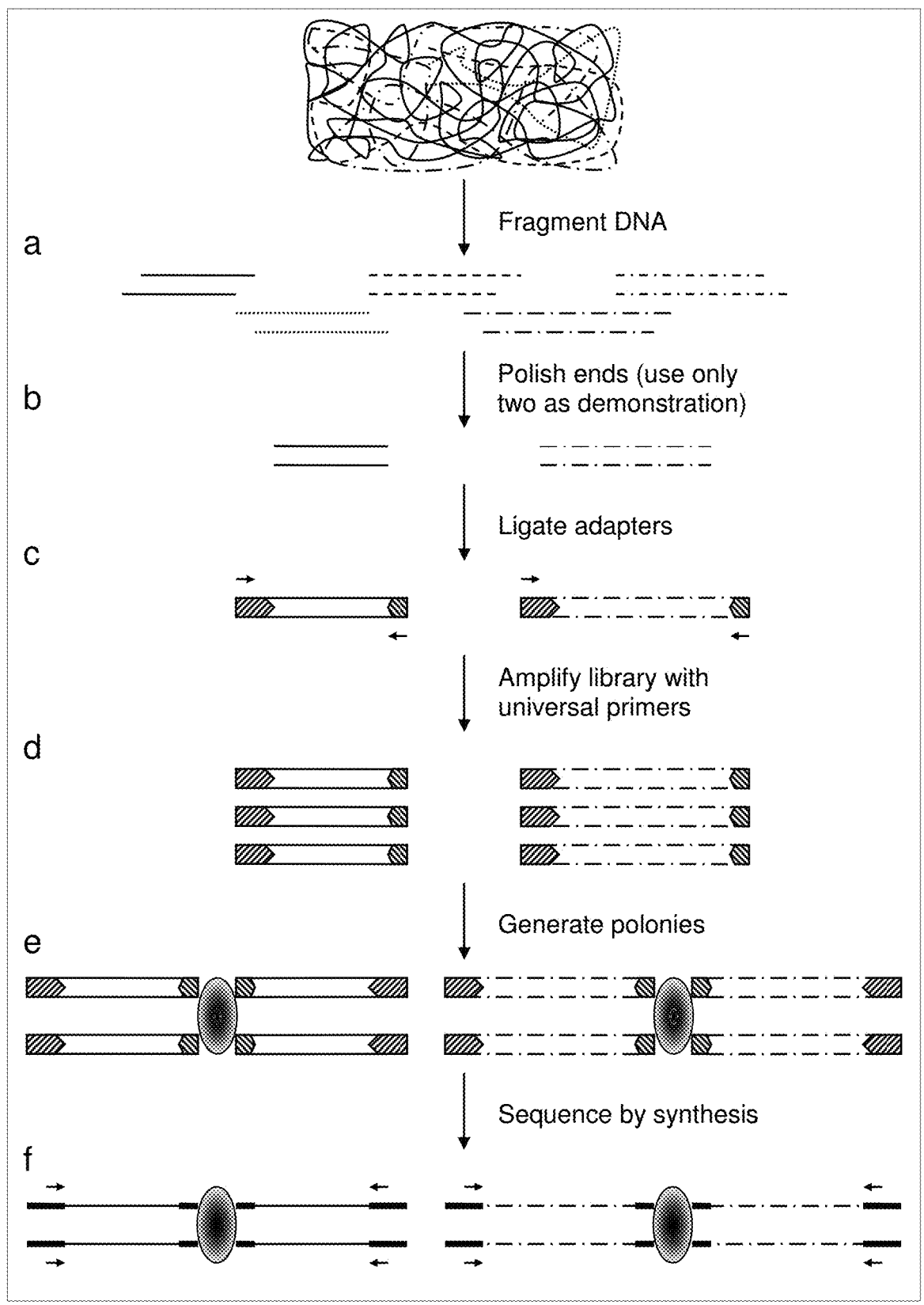
FIG. 1 is a generic flow diagram illustrating the molecular process of high throughput nucleic acid sequencing.

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Albers et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes IX, Oxford University Press: New York, 2007. The nomenclature for DNA bases as set forth at 37 CFR § 1.822 is used.

An "allele" refers to an alternative sequence at a particular locus; the length of an allele can be as small as 1 nucleotide base. Allelic sequence can be denoted as nucleic acid sequence or as amino acid sequence that is encoded by the nucleic acid sequence.

A "locus" is a position on a genomic sequence that is usually found by a point of reference; e.g., a short DNA sequence that is a gene, or part of a gene or intergenic region. A locus may refer to a nucleotide position at a reference point on a chromosome, such as a position from the end of the chromosome. The ordered list of loci known for a particular genome is called a genetic map. A variant of the DNA sequence at a given locus is called an allele and variation at a locus, i.e., two or more alleles, constitutes a polymorphism. The polymorphic sites of any nucleic acid sequence can be determined by comparing the nucleic acid sequences at one or more loci in two or more germplasm entries.

As used herein, a "nucleic acid sequence" comprises a contiguous region of nucleotides at a locus within the genome. Further, a nucleic acid sequence, as used herein, may comprise one or more haplotypes, portions of one or more haplotypes, one or more genes, portions of one or more genes, one or more QTL, and portions of one or more QTL. In addition, a plurality of nucleic acid sequences can comprise one or more haplotypes, portions of one or more haplotypes, one or more genes, portions of one or more genes, one or more QTL, and portions of one or more QTL. The sequence may originate from a DNA or RNA template, either directly or indirectly (i.e., cDNA obtained from reverse transcription of mRNA).

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found, or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms. In addition, the presence, absence, or variation in copy number of the preceding may comprise a polymorphism.

As used herein, "nucleic acid effect estimate" means a predicted effect estimate for a nucleic acid sequence reflecting association with one or more phenotypic traits, wherein said associations can be made de novo or by leveraging historical nucleic acid sequence-trait association data.

As used herein, "breeding value" means a calculation based on nucleic acid sequence effect estimates and nucleic acid sequence frequency values, the breeding value of a specific nucleic acid sequence relative to other nucleic acid sequences at the same locus (i.e., haplotype window), or across loci (i.e., haplotype windows), can also be determined. In other words, the change in population mean by fixing said nucleic acid sequence is determined. In addition, in the context of evaluating the effect of substituting a specific region in the genome, either by introgression or a transgenic event, breeding values provide the basis for comparing specific nucleic acid sequences for substitution effects. Also, in hybrid crops, the breeding value of nucleic acid sequences can be calculated in the context of the nucleic acid sequence in the tester used to produce the hybrid.

As used herein, "genotype" is the actual nucleic acid sequence at a locus in an individual plant. As opposed to a genetic marker such as a SNP, where the genotype comprises a single nucleotide, the genotype identified with the present invention is a plurality of nucleotides, where the length of the genotype is contingent on the length of the nucleic acid sequence. Notably, a genetic marker assay as known in the art (e.g., SNP detection via TaqMan) detects only two alleles. An advantage of the present invention is the ability to directly query all four nucleotides (adenine, A; thymine, T; cytosine, C; and guanine, G) simultaneously at any one nucleotide position. That is, for any one base pair position, there will be twice the information when using direct nucleic acid sequencing versus genetic marker assays. This can be very important in determining whether two lines share DNA that is identical by descent. With a SNP genotype, one can only assess whether a pair of alternative nucleic acid bases exist at a single nucleotide locus. For example, one might query whether two lines have a C or a T at a single nucleotide locus and find that one line has a C but the other has neither. However, unlike directly assessing the sequence at the single nucleotide locus, the genetic marker assay will not distinguish a failed reaction or whether an alternative base, such as an adenine or guanidine, is present at that locus. Therefore, the present invention provides greater certainty whether a given region is identical by descent by observing the nucleic acid sequence for that region.

As used herein, a nucleic acid sequence can comprise 1 or more nucleotides (for example, 2 or more nucleotides, 25 or more nucleotides, 250 or more nucleotides, 1,000 or more nucleotides, even 20,000 or more nucleotides). In certain embodiments, adjacent nucleic acid sequence fragments can be ligated in vitro or aligned in silico for the purpose of obtaining a longer nucleic acid sequence. As used herein, a nucleic acid sequence from each of two or more individual plants from the same genomic region, that may or may not be associated with one or more phenotypic trait values, provides the basis for decisions related to germplasm improvement activities, wherein one or more loci can be evaluated. Knowing whether two sequences at a locus are completely identical or if they contain combinations of identical and non-identical loci can aid in determining whether the loci have the same trait value, are linked to the same traits or are identical by descent. Therefore in another aspect, one or more nucleic acid sequences from one or more individual plants that are associated with a phenotypic trait value can provide the basis for decisions related to germplasm improvement activities.

As used herein, the term "haplotype" means a chromosomal region within a haplotype window. Typically, the unique marker fingerprint combinations in each haplotype window define and differentiate individual haplotypes for that window. As used herein, a haplotype is defined and differentiated by one or more nucleic acid sequences at one or more loci within a "haplotype window."

As used herein, the term "haplotype window" means a chromosomal region that is established by statistical analyses known to those of skill in the art and is in linkage disequilibrium. In the art, identity by state between two inbred individuals (or two gametes) at one or more molecular marker loci located within this region is taken as evidence of identity-by-descent of the entire region, wherein each haplotype window includes at least one polymorphic molecular marker. As used herein, haplotype windows are defined by two or more nucleic acid sequence genotypes. Haplotype windows can be mapped along each chromosome in the genome and do not necessarily need to be contiguous. Haplotype windows are not fixed per se and, given the ever-increasing amount of nucleic acid sequence information, this invention anticipates the number and size of haplotype windows to evolve, with the number of windows increasing and their respective sizes decreasing, thus resulting in an ever-increasing degree confidence in ascertaining identity by descent based on the identity by state of genotypes. Haplotype windows are useful in delineating nucleic acid sequences of interest because these genomic regions tend to be inherited as linkage blocks and thus are informative for association mapping and for tracking across multiple generations.

As used herein, "phenotype" means the detectable characteristics of a cell or organism which can be influenced by genotype.

As used herein, "marker" means a detectable characteristic that can be used to discriminate between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics. As used herein, "genetic marker" means polymorphic nucleic acid sequence or nucleic acid feature.

As used herein, "marker assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "consensus sequence" means a constructed DNA sequence which identifies single nucleotide and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, "linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are said to be "genetically linked" when they are in linkage disequilibrium.

As used herein, "quantitative trait locus (QTL)" means a locus that controls to some degree numerically representable traits that are usually continuously distributed.

As used herein, "complexity reduction" refers to methods to reduce the complexity of a nucleic acid sample, such as by restriction enzyme digestion, reverse transcription, targeted amplification by PCR methods, or random amplification by PCR methods. Complexity reduction can be performed on total genomic nucleic acids or a subset thereof. In a preferred aspect, a method with reproducible results will be used. Methods for complexity reduction are included in WO 06/137734, WO 06/137733, and EP 0 534 858 which are specifically incorporated herein by reference in their entirety.

As used herein, "DNA tag" means a short segment of DNA used as an identifier for a nucleic acid sample. A DNA tag, also known as a molecular barcode, can range from about 2 to about 20 base pairs in length and can be added during complexity reduction of the template nucleic acid sample(s). For examples, sets of DNA tags are available in U.S. Pat. No. 7,157,564. The tag can be identified via sequencing or microarray methods as described in EP 1 724 348. In other embodiments, such as in the case of oligonucleotides mass tags, mass spectrometry methods have been used to differentiate tags (Zhang et al. PNAS 2007 104:3061-3066). Further, molecular barcodes have been developed for detection by other imaging platforms, including surface plasmon resonance, fluorescent, or Raman spectroscopy, as described in U.S. Patent Application 2007/0054288. In another embodiment, spike-in tags of RNA or protein have been used which are distinct from molecules of the target sample and are co-analyzed with a plurality of samples for the purpose of sample discrimination, methods of which are included in WO 03/052101. In a preferred embodiment of this invention, the identity of the tag is assessed by sequencing either directly before or directly after the sequencing of a trait locus. In this way, the sequence of the tag conjugated to the sequence of the locus and can be used to maintain a linkage between the locus sequence and the sample origin. In another embodiment, the tag may be combinatorial or hierarchical. For example one portion of the tag may indicate multiple nucleic acids are from the same sample and another portion of the tag may indicate the nucleic acids were derived from different subsamples. The number of hierarchical levels or combinations of tags is only limited by the amount of sequencing which can be dedicated to the DNA tag vs. the trait locus.

As used herein, a "tagged sample" means a sample of nucleic acid to which the same tag has been attached to each individual nucleic acid in the sample. As used herein, a tagged sample includes a samples tagged with a hierarchical or combinatorial tag, wherein at least a portion of the tag is identical and attached to each nucleic acid sequence in the sample.

As used herein, an "allele-specific tag" is a DNA tag that corresponds to a particular allele in the target sequence. In a preferred embodiment, only the allele-specific tag, rather than the polymorphism plus any linked DNA tags, needs to be sequenced to be able to genotype the corresponding polymorphism.

As used herein, "nucleic acid sequencing" means the determination of the order of nucleotides in a sample of nucleic acids, wherein nucleic acids include DNA and RNA molecules. "High throughput nucleic acid sequencing" means an automated and massively parallel approach for the determination of nucleotides in a sample of nucleic acids wherein examples of high throughput nucleic acid sequencing technology include, but are not limited to, platforms provided by 454 Life Sciences, Agencourt Bioscience, Applied Biosystems, LI-COR Biosciences, Microchip Biotechnologies, Network Biosystems, NimbleGen Systems, Illumina, and VisiGen Biotechnologies, comprising but not limited to formats such as parallel bead arrays, sequencing by synthesis, sequencing by ligation, capillary electrophoresis, electronic microchips, "biochips," microarrays, parallel microarrays, and single-molecule arrays, as reviewed by Service (Science 2006 311:1544-1546).

As used herein, "aligning" or "alignment" of two or more nucleic acid sequences is the comparison of the nucleic acid sequences found at the same locus. Several methods of alignment are known in the art and are included in most of the popular bioinformatics packages.

As used herein, the term "primer" means a single strand of synthetic oligonucleotide, preferably from about 10 to about 120 nucleotides, which can be synthesized chemically or assembled from several chemically synthesized oligonucleotides. As used herein, primers may be used to initiate sequencing reactions and polymerase reactions, such as in gap fill reactions and PCR. As used herein, a primer will hybridize under the assay conditions specifically to a desired target sequence. As used herein, primers may be used to introduce a DNA tag, to introduce chemically modified bases, such as biotin labeled bases, or to introduce a hybridization sequence that can subsequently be used for capture, such as capture to a sequencing matrix or to an avidin-containing surface.

As used herein, the term "adapters" means a double stranded nucleic acid molecule of a known composition, typically about 10 to 120 base pairs in length, which are designed such that they can be ligated, for example through the use of a DNA ligase, to one or both ends of a second nucleic acid molecule(s). Adapters can be designed to be ligated to the blunt end of a nucleic acid (blunt end adapters) or by first annealing to a specific overhang sequence and then ligated. In this embodiment, adapters may be used to provide primer sites, to tag a nucleic acid with a DNA tag, to provide sequences that enable hybridization for the purposes of capture and to add chemically modified nucleic acid sequences such as biotin containing adapters.

As used herein, the term "ligation" means the biochemical reaction catalyzed by the enzyme ligase wherein two DNA molecules are covalently joined.

As used herein, "DNA amplification" means the in vitro synthesis of double stranded DNA through the use of a DNA polymerase. Typically, this is accomplished in a polymerase chain reaction (PCR) assay but may also include other methods such as a gap-fill reaction, mis-match repair, Klenow reaction, etc. DNA amplification is used to provide detectable or excess amounts of a specific DNA. It can also be used to incorporate into a target nucleic acid, hybridized probes, annealed adaptors and primers which may include specific functionality or information.

As used herein, the term "transgene" means nucleic acid molecules in form of DNA, such as cDNA or genomic DNA, and RNA, such as mRNA or microRNA, which may be single or double stranded.

As used herein, the term "inbred" means a line that has been bred for genetic homogeneity.

As used herein, the term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines.

As used herein, the term "tester" means a line used in a testcross with another line wherein the tester and the lines tested are from different germplasm pools. A tester may be isogenic or nonisogenic.

As used herein, the term "corn" means *Zea mays* or maize and includes all plant varieties that can be bred with corn, including wild maize species. More specifically, corn plants from the species *Zea mays* and the subspecies *Zea mays* L. ssp. *Mays* can be genotyped using the compositions and methods of the present invention. In an additional aspect, the corn plant is from the group *Zea mays* L. subsp. *mays* Indentata, otherwise known as dent corn. In another aspect, the corn plant is from the group *Zea mays* L. subsp. *mays* Indurata, otherwise known as flint corn. In another aspect, the corn plant is from the group *Zea mays* L. subsp. *mays* Saccharata, otherwise known as sweet corn. In another aspect, the corn plant is from the group *Zea mays* L. subsp. *mays* Amylacea, otherwise known as flour corn. In a further aspect, the corn plant is from the group *Zea mays* L. subsp. *mays* Everta, otherwise known as pop corn. *Zea* or corn plants that can be genotyped with the compositions and methods described herein include hybrids, inbreds, partial inbreds, or members of defined or undefined populations.

As used herein, the term "soybean" means *Glycine max* and includes all plant varieties that can be bred with soybean, including wild soybean species. More specifically, soybean plants from the species *Glycine max* and the subspecies *Glycine max* L. ssp. max or *Glycine max* ssp. *formosana* can be genotyped using the compositions and methods of the present invention. In an additional aspect, the soybean plant is from the species *Glycine soja*, otherwise known as wild soybean, can be genotyped using these compositions and methods. Alternatively, soybean germplasm derived from any of *Glycine max, Glycine max* L. ssp. max, *Glycine max* ssp. *Formosana*, and/or *Glycine soja* can be genotyped using compositions and methods provided herein.

As used herein, the term "comprising" means "including but not limited to".

As used herein, the term "elite line" means any line that has resulted from breeding and selection for superior agronomic performance. An elite plant is any plant from an elite line.

In accordance with the present invention, Applicants have discovered methods for making breeding decisions genotypically on nucleic acid sequences per se. For example, the methods of the present invention provide for direct, sequence-based analysis instead of using genetic markers as indirect tools for selecting a locus of interest. Further, the methods of the present invention allow for improved flexibility in using nucleic acid information in a breeding program, wherein the entire genome of a plant or animal can be queried without reliance on pre-determined genetic markers and the development of genetic marker detection assays. In addition, any length of sequence from any locus can be leveraged to 1) determine genotype-trait associations, 2) discriminate between two or more lines, 3) predict line performance or hybrid performance and, ultimately, 4) provide the basis for decisions in activities related to germplasm improvement.

Molecular breeding is often referred to as marker-assisted selection (MAS) and marker-assisted breeding (MAB), wherein MAS refers to making breeding decisions on the basis of molecular marker genotypes for at least one locus and MAB is a general term representing the use of molecular markers in plant breeding. In these types of molecular breeding programs, genetic marker alleles can be used to identify plants that contain the desired genotype at one marker locus, several loci, or a haplotype, and that would therefore be expected to transfer the desired genotype, along with an associated desired phenotype, to their progeny. Markers are highly useful in plant breeding because, once established, they are not subject to environmental or epistatic interactions. Furthermore, certain types of markers are suited for high throughput detection, enabling rapid identification in a cost effective manner.

Marker discovery and development in crops provides the initial framework for applications to MAB (U.S. Pat. No. 5,437,697; U.S. Patent Applications 2005000204780, 2005000216545, 2005000218305, and 2006000504538). The resulting "genetic map" is the representation of the relative position of characterized loci (DNA markers or any other locus for which alleles can be identified) along the chromosomes. The measure of distance on this map is relative to the frequency of crossover events between sister chromatids at meiosis. As a set, polyallelic markers have served as a useful tool for fingerprinting plants to inform the degree of identity of lines or varieties (U.S. Pat. No. 6,207,367). These markers form the basis for determining associations with phenotype and can be used to drive genetic gain. The implementation of MAS, wherein selection decisions are based on marker genotypes, is dependent on the ability to detect underlying genetic differences between individuals.

Because of allelic differences in these molecular markers, QTL can be identified by statistical evaluation of the genotypes and phenotypes of segregating populations. Processes to map QTL are well-described (WO 90/04651; U.S. Pat. Nos. 5,492,547, 5,981,832, 6,455,758; reviewed in Flint-Garcia et al. 2003 Ann. Rev. Plant Biol. 54:357-374). Using markers to infer phenotype in these cases results in the economization of a breeding program by substitution of costly, time-intensive phenotyping with genotyping. Marker approaches allow selection to occur before the plant reaches maturity, thus saving time and leading to more efficient use of plots. In fact, selection can even occur at the seed level so only preferred seeds are planted (U.S. Patent Applications 2005000213435 and 2007000680611). Further, breeding programs can be designed to explicitly drive the frequency of specific, favorable phenotypes by targeting particular genotypes (U.S. Pat. No. 6,399,855). Fidelity of these associations may be monitored continuously to ensure maintained predictive ability and, thus, informed breeding decisions (U.S. Patent Application 2005/0015827).

This process has evolved to the application of markers as a tool for the selection of "new and superior plants" via introgression of preferred loci as determined by statistical analyses (U.S. Pat. No. 6,219,964). Marker-assisted introgression involves the transfer of a chromosomal region, defined by one or more markers, from one germplasm to a second germplasm. The initial step in that process is the localization of the genomic region or transgene by gene mapping, which is the process of determining the position of a gene or genomic region relative to other genes and genetic markers through linkage analysis. The basic principle for linkage mapping is that the closer together two genes are on a chromosome, the more likely they are to be inherited together. Briefly, a cross is generally made between two genetically compatible but divergent parents relative to the traits of interest. Genetic markers can then be used to follow the segregation of these traits in the progeny from the cross, often a backcross (BC1), $F_2$, or recombinant inbred population.

Historically, genetic markers were not appropriate for distinguishing identity by state or by descent. It has long been recognized that genes and genomic sequences may be identical by state (i.e., identical by independent origins; IBS) or identical by descent (i.e., through historical inheritance from a common progenitor; IBD) which has tremendous bearing on studies of linkage disequilibrium and, ultimately, mapping studies (Nordborg et al. 2002 Trends Gen. 18:83-90). Notably, newer classes of markers such as SNPs (single nucleotide polymorphisms), are more diagnostic of origin. The likelihood that a particular SNP allele is derived from independent origins in the extant populations of a particular species is very low. Polymorphisms occurring in linked genes are randomly assorted at a slow, but predictable rate, described by the decay of linkage disequilibrium or, alternatively, the approach of linkage equilibrium. Consequences of this well-established scientific discovery are that long stretches of coding DNA, defined by a specific combination of polymorphisms, are very unique and extremely improbable of existing in duplication except through linkage disequilibrium, which is indicative of recent co-ancestry from a common progenitor. The probability that a particular genomic region, as defined by some combination of alleles, indicates absolute identity of the entire intervening genetic sequence is dependent on the number of linked polymorphisms in this genomic region, barring the occurrence of recent mutations in the interval. Such loci are also referred to as haplotype windows. Each haplotype within that window is defined by specific combinations of alleles; the greater the number of alleles, the greater the number of potential haplotypes, and the greater the certainty that identity by state is a result of identity by descent at that region. The present invention permits the direct determination of IBD by using direct nucleic acid sequence information, rather than inferred by marker information.

During the development of new lines, ancestral haplotypes are maintained through the process and are typically thought of as 'linkage blocks' that are inherited as a unit through a pedigree. Further, if a specific haplotype has a known effect, or phenotype, it is possible to extrapolate its effect in other lines with the same haplotype. Currently, haplotypes are identified and tracked in germplasm using one or more diagnostic markers for that haplotype window. The present invention provides a method to directly identify haplotypes by using nucleic acid sequence information. Further, by using direct sequence information, more polymorphisms within any genomic region may be identified versus using only genetic markers, thus resulting in the identification of additional haplotypes. One can also better assess haplotypes that may share identity by descent. By discriminating haplotypes on a deeper level, greater fidelity in haplotype-phenotype associations can be gained. In another aspect, exotic germplasm can be queried for novel haplotypes by using direct sequence information, thus enabling the identification and subsequent leveraging of unique haplotypes.

In another approach, regions of IBD can be queried across at least one germplasm pool in order to assess genetic diversity. For example, allelic variants have been queried in order to infer genetic bottlenecks in the domestication of crop plants (reviewed in Doebley et al. 2006 Cell 127:1309-1321). However, using a marker platform to query diversity may be limiting since a single marker queries only a single position in the sequence.

Further, one theory of heterosis predicts that regions of IBD between the male and female lines used to produce a hybrid will reduce hybrid performance. Identity by descent has historically been inferred from patterns of marker alleles in different lines, wherein an identical string of markers at a series of adjacent loci may be considered identical by descent if it is unlikely to occur independently by chance. Analysis of marker fingerprints in male and female lines can identify regions of IBD. In the present invention, the genome can be directly queried for at least one locus within the genome to evaluate IBD between lines. Knowledge of these regions can inform the choice of hybrid parents, since avoiding IBD in hybrids is likely to improve performance. This knowledge may also inform breeding programs in that crosses could be designed to produce pairs of inbred lines (one male and one female) that show little or no IBD.

In one aspect of the present invention, heterosis is evaluated for at least one genomic region, wherein heterozygosity between parents in a cross as determined on an allele basis can be presumed to confer a phenotypic advantage. In another aspect of the present invention, methods are provided to evaluate heterosis in terms of genomic synteny, wherein non-colinearity for at least one locus can result in a heterotic advantage and improved performance in the hybrid.

Markers have traditionally been used to fingerprint lines and thus provide estimates of genetic purity, facilitate QA/QC operations, and assess genetic diversity. The present invention improves upon traditional marker protocols by providing methods to directly assess base pair sequences, instead of estimating underlying sequence identity from a single base position as with traditional marker protocols. For example, a typical biallelic SNP marker provides information on only one base pair position and it can only distinguish between 2, rather than 4, nucleotides.

The methods of the present invention take advantage of recent breakthroughs in high throughput sequencing to provide novel methods for molecular breeding. High throughput (HT) sequencing methodologies have recently been developed whereby information can be generated for 100 MB or more of sequence in a single sequencing machine run. It is contemplated that any commercially available HT sequencing technology, or any other commercially available nucleic acid sequencing platform that may be developed in the future, can be employed as long as the platform is capable of determining the sequence of a single nucleic acid molecule. Non-limiting examples of commercially available HT sequencing technologies are provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Commercially available HT sequencing technologies are also reviewed in Service (Science 2006 311:1544-1546), which is incorporated herein by reference in its entirety. In essence the Illumina Genome Analyzer, 454 Flex and the ABI Solid technology are able to determine the sequence of a single DNA molecule although that molecule may be amplified in the process. Some of these examples employ sequencing by synthesis although this is not a pre-requisite. Preferred HT sequencing platforms will generate 100 megabases, 1 gigabase or even more sequence information per run. Highly preferred HT sequencing platforms will simultaneously determine the sequence on the maximum number of individual DNA molecules. Such systems are said to be highly parallel. For this reason, the Illumina Genome Analyzer platform is generally preferred because it can sequence many more DNA molecules by generating only a small read per molecule. Platforms which generate longer reads on fewer sequences will work but may present additional challenges for time and cost efficiency.

Direct determination of the polymorphic nucleotides has key advantages over marker technologies. Although marker technologies are generally robust, they can still incorrectly report an underlying sequence, be subject to noise, and be subject to failure. Further, a marker may not span the actual genomic region of interest and, depending on the degree of linkage to the genomic region of interest, lose value in breeding populations due to recombination and loss of the linkage. Direct determination of the nucleic acid sequences overcomes the inherent limitations of a marker based system by sequencing through not just the nucleotide(s) of interest but the surrounding sequences as well. In addition, the present invention provides methods for "indirect" polymorphism detection wherein allele-specific tags are used that are immediately adjacent to the SNP (FIG. 5) so the sequencing reaction only needs to be completed as far as the tag, which is especially useful for technologies generating short reads. Indirect sequencing still overcomes the shortcomings of typical markers' tendency to be linked, vs. comprising, causal polymorphisms since the tag is essentially physically linked to the SNP. Use of nucleic acid sequencing also provides more sequence information about the loci that correlate to traits of importance, which will help breeders better understand and utilize the loci or traits. Furthermore, direct determination of nucleic acid sequences may eliminate the need for extensive up-front sequencing for marker development.

In one embodiment, the method of the present invention comprises sequencing the whole genome of one plant, comparing the sequenced genome to the genotype of a second plant and then making a decision to cross them, select either one or both to advance, or test the combination of the two. Alternatively, the whole genome information can be used to develop pedigrees by grouping lines that share similarities and separating lines on the basis of genetic differences in order to leverage heterosis. The whole genome sequence provides the complete listing of polymorphic nucleotides and the complete listing of haplotypes.

The HT sequencing technology as described in the public domain is enabling yet still inherently limited in its application to plant genotyping, even with the ability to sequence 100 megabases or even 1 gigabases of sequence per sample. The limitation arises from the need to sequence 10,000s of thousands of individuals or lines needed to support a modern breeding program. The large number of individuals or lines are needed to identify rare recombinants between two loci or the sub-population with the highest frequency of favorable alleles at multiple loci. The ability to sequence the whole genomes of such a large number of individuals is still impractical. A means to reduce the genome to a smaller number of informative polymorphic regions is needed as well as a means to combine samples from multiple individuals into a smaller number of sequencing runs or reactions. One aspect of this invention is the use of a reproducible method to reduce the complexity of a whole genome to a representative subset of sequences which can be analyzed, compared and used for plant breeding decisions. An additional aspect of this invention is the ability to apply DNA tagging so that multiple samples can be combined in a single sequencing run. The sequences from the combined samples that are determined in parallel in a single run can then be de-convoluted and tracked back to the individual plant or plant pool which they originated.

In one aspect, the present invention provides subsets of total genomic DNA or RNA for nucleic acid sequencing such that a reduced representation sample is obtained to narrow the target for sequencing, i.e., to coding regions or regions including at least one polymorphism of interest. These subsets may sometimes be referred to as reduced complexity samples or libraries.

In another aspect of this invention, the reduced representation sample is targeted to or limited to one or more selected regions, or loci, in the genome. The selected loci can be selected based on one or more associations with one or more traits or performance characteristics or they can be a representative subset of the all loci within a genome, such as a subset evenly spaced along the chromosomes and which are segregating in the target breeding population. A preferred subset of the loci are polymorphic loci. A polymorphic locus is defined by one or more nucleotides that vary between a pair of or multiple individuals or lines. Any type of polymorphic locus may be used with this technology including but not limited to sequence length polymorphisms, repetitive sequence length polymorphisms, restriction site polymorphisms and single nucleotide polymorphisms. Single nucleotide polymorphisms are detected in a preferred embodiment of this invention. The sequence of a targeted locus can be determined by priming the locus to synthesize a complementary oligonucleotide and then directly sequencing the complementary oligonucleotide. The targeted regions can be synthesized through a gap fill reaction, primer extension reaction, a polymerase chain reaction or a combination of these reactions. Alternatively, in the case of polymorphic targeted loci, mis-match repair enzymes or ribozymes or other such nucleotide specific enzymes can be used to specifically repair a complementary oligonucleotide that is mis-matched at the polymorphic nucleotide. Once the complementary nucleotide has been extended, amplified, repaired or gap-filled, the sequence of the in vitro generated oligonucleotide can be determined and represents the sequence of the polymorphic locus. Any of these methods can be employed to directly determine the nucleotide sequence of one or both strands of one or many nucleotide regions. Since the high throughput sequencing methodologies can generate greater than 100 MB of sequence information in a single run, oligonucleotides from large number of loci can be combined and sequenced simultaneously such that the sequences of large numbers of loci can be determined in parallel in one sequencing reaction. In such an embodiment, the invention provides high-throughput and cost effective methods for the direct determination of polymorphic, or non-polymorphic, nucleotides.

In another aspect, a reduced representation sample can be prepared that consists of a specific class of genome fragments. In one preferred embodiment, a sample is prepared using restriction enzymes. For the purpose of comparing at least two plants of a species, each sample is prepared by digesting with one or more restriction endonucleases, fractionating the digested DNA fragments based on size of nucleotide sequence and comparing the sequence of a fragments in a fraction. More particularly, the method of identifying at least one locus in genomic DNA comprises digesting total genomic DNA from at least two variants of a eukaryotic species with a methylation sensitive endonuclease to provide a pool of digested DNA fragments. The average nucleotide length of fragments is smaller for DNA regions characterized by a lower percent of 5-methylated cytosine. Such fragments are separable, e.g. by gel electrophoresis, based on nucleotide length. A fraction of DNA with less than average nucleotide length is separated from the pool of digested DNA. As compared to coding sequence, repetitive sequence is more likely to comprise 5-methylated cytosine, e.g. in -CG- and -CNG- sequence segments. In a preferred aspect of the method, genomic DNA from at least two different inbred varieties of a crop plant is digested with a with a methylation sensitive endonuclease selected from the group consisting of Aci I, Apa I, Age I, Bsr F I, BssH II, Eag I, Eae I, Hha I, HinP1 I, Hpa II, Msp I, MspM II, Nar I, Not I, Pst I, Pvu I, Sac II, Sma I, Stu I and Xho I to provide a pool of digested DNA which can be physically separated, e.g. by gel electrophoresis. Comparable size fractions of DNA are obtained from digested DNA of each of said varieties and then sequenced.

In another embodiment, RNA can be used as a reduced representation of the genome, i.e. the subset of the genome which is expressed. The RNA may be polyA RNA, small RNA or other RNA fractions which may be used directly after extraction or experimentally manipulated to further reduce complexity or improve reproducibility. Prior to sequencing, the RNA is converted by reverse transcription methods to cDNA which can be directly sequenced or experimentally manipulated to further reduce complexity or improve reproducibility.

In a preferred embodiment of this invention, multiple nucleic acid samples can be combined into a sample multiplex, i.e. pool, and sequenced in parallel in the same run to maximize sample throughput per sequencing run. To achieve this, a DNA tag, comprising one or more nucleotides unique for that sample, is added to the nucleic acid prepared from an individual sample. Typical DNA tags comprise 1 to 10 nucleotides but can extend to any length as long as the tag does not interfere with the ability to determine the sample sequence. For example, a DNA tag of 2 nucleotides can be use to separate a mixture of 16 samples. DNA tags of 3, 4, 5 or 6 nucleotides can be used to separate mixtures of 64, 256, 1024 or 4096 samples, and so on. Shorter DNA tags place less constraints on sequence read length but limit the number of samples which can be mixed. In one embodiment of the invention, the DNA tags are simply synthesized as part of one or both PCR primers and then incorporated in a PCR reaction. In another aspect, the DNA tag can be ligated onto the sample nucleic acids using a DNA ligase. After fully incorporating a DNA tag into the nucleic acid sample, multiple DNA preparations, each with a unique tag, can be multiplexed, i.e. pooled or combined. The multiplexed mixtures are then subjected to a single HT sequencing reaction. The number of samples that are multiplexed is based on optimally using the full sequencing capacity of a single sequencing run. Parameters that influence the complexity of a sample mixture include the number of loci being assessed, the size of the loci, the information content per run of the HT platform, the length of the DNA tag, the presence, if any, of an adapter or primer sequence and the read length of a given sequence. The level of multiplexing can be balanced to achieve optimum cost per sample, redundancy per sequence read. The minimum length of a single sequence read needs to be sufficient to read a sample DNA tag (for example, 2-5 nucleotides, depending on the number of samples which are pooled), a sequence specific tag (6-20 nucleotides) and one or more adjacent nucleotides. After the HT sequencing reaction, sequences with the same DNA tag are first separated logically into separate pools which represent the individual or line or pool which the DNA was extracted. The sequences with identical DNA tags can then be read to determine the nucleotide identity within the loci which were selected to be queried.

In this invention, the sequence of nucleic acids can be associated to traits of interest or to plant performance and then used to make selections of parents, progeny or testers. Sequences will be useful if they are genetically linked to the trait or performance characteristic. Typically, they are genetically linked if they are causative for the trait or performance characteristic or are closely physically linked to the trait or performance loci. In the case of physically linked sequences, no knowledge of the gene(s) and/or causative variation for the trait or performance information is required. One only needs to determine the sequence of the physically linked nucleotides. Once a sequence has been genetically linked to a trait or performance character, the sequence of the nucleic acids can be directly used to select parents, progeny or testers which will exemplify that trait or performance without the need to first measure the trait or performance characteristic. The knowledge of the nucleotide sequences can also be used to fingerprint a plant or line and be used to measure genetic similarity/distance among plants or lines and to build pedigrees. The pedigrees can then be used to make selections of parents or to manage the diversity in a germplasm pool.

In another embodiment, plants can be screened for one or more markers, such as nucleic acid sequences, using high throughput, non-destructive seed sampling. In a preferred aspect, seed is sampled in this manner and only seed with at least one genotype of interest is advanced. Apparatus and methods for the high-throughput, non-destructive sampling of seeds have been described which would overcome the obstacles of statistical samples by allowing for individual seed analysis. For example, published U.S. Patent Applications US 2006/0042527, US 2006/0046244, US 2006/0046264, US 2006/0048247, US 2006/0048248, US 2007/0204366, and US 2007/0207485, which are incorporated herein by reference in their entirety, disclose apparatus and systems for the automated sampling of seeds as well as methods of sampling, testing and bulking seeds.

As provided by the present invention, the knowledge of nucleic acid sequences can be applied to make decisions at multiple stages of the breeding program:

a) Among segregating progeny, as a pre-selection method, to increase the selection index and drive the frequency of favorable nucleic acid sequences among breeding populations, wherein pre-selection is defined as selection among offspring of a breeding cross based on the genotype of these progenies at a selected set of two or more nucleic acid sequences at one or more loci as determined by HT sequencing, and leveraging of nucleic acid sequence-trait associations identified in previous breeding crosses.

b) Among segregating progeny from a breeding population, to increase the frequency of the favorable nucleic acid sequences for the purpose of line or variety development.

c) Among segregating progeny from a breeding population, to increase the frequency of the favorable nucleic acid sequences prior to QTL mapping within this breeding population.

d) For hybrid crops, among parental lines from different heterotic groups to predict the performance potential of different hybrids.

In another embodiment, the present invention provides a method for improving plant germplasm by accumulation of nucleic acid sequences of interest in a germplasm comprising determining nucleic acid sequences for at least two loci in the genome of a species of plant, and associating the nucleic acid sequences with at least one trait, and using this nucleic acid sequence effect estimates to direct breeding decisions. These nucleic acid sequence effect estimates can be derived using historical nucleic acid sequence-trait associations or de novo from mapping populations. The nucleic acid sequence effect estimates for one or more traits provide the basis for making decisions in a breeding program. This invention also provides an alternative basis for decision-making using breeding value calculations based on the estimated effect and frequency of nucleic acid sequences in the germplasm. Nucleic acid sequence breeding values can be used to rank a specified set of nucleic acid sequences. In the context of the specified set of nucleic acid sequences, these breeding values form the basis for calculating an index to rank the alleles both within and between loci.

For example, any given chromosome segment can be represented in a given population by a number of nucleic acid sequences that can vary from 1 (region is fixed), to the size of the population times the ploidy level of that species (2 in a diploid species), in a population in which every chromosome has a different nucleic acid sequence. Identity-by-descent among nucleic acid sequences carried by multiple individuals in a non-fixed population will result in an intermediate number of different nucleic acid sequences and possibly a differing frequency among the different nucleic acid sequences. New nucleic acid sequences may arise, through recombination at meiosis between existing nucleic acid sequences in heterozygous progenitors. The frequency of each nucleic acid sequence may be estimated by several means known to one versed in the art (e.g. by direct counting, or by using an EM algorithm). Let us assume that "k" different nucleic acid sequences, wherein a nucleic acid sequence represents at least one nucleotide and may constitute an allele or haplotype, identified as "$n_i$" (i=1, . . . , k), are known, that their frequency in the population is "$f_i$" (i=1, . . . , k), and for each of these nucleic acid sequences we have an effect estimate "$Est_i$" (i=1, . . . , k). If we call the "breeding value" ($BV_i$) the effect on that population of fixing that nucleic acid sequence, then this breeding value corresponds to the change in mean for the trait(s) of interest of that population between its original state of haplotypic distribution at the window and a final state at which nucleic acid sequence "$n_i$" encounters itself at a frequency of 100%. The breeding value of $n_i$ in this population can be calculated as:

$$BV_i = Est_i - \sum_{i=1}^{k} Est_i f_i$$

One skilled in the art will recognize that nucleic acid sequences that are rare in the population in which effects are estimated tend to be less precisely estimated, this difference of confidence may lead to adjustment in the calculation. For example one can ignore the effects of rare nucleic acid sequences, by calculating breeding value of better known nucleic acid sequence after adjusting the frequency of these (by dividing it by the sum of frequency of the better known nucleic acid sequences). One could also provide confidence intervals for the breeding value of each nucleic acid sequences.

This breeding value will change according to the population for which it is calculated, as a function of difference of nucleic acid sequence frequencies. The term population can then assume different meanings, below are two examples of special cases. First, it can be a single inbred line in which one intend to replace its current nucleic acid sequence $n_j$ by a new nucleic acid sequence $n_i$, in this case $BV_i=Est_i-Est_j$. Second, it can be a F2 population in which the two parental nucleic acid sequence $n_i$ and $n_j$ are originally present in equal frequency (50%), in which case $BV_i=\frac{1}{2}(Est_i-Est_j)$.

These statistical approaches enable nucleic acid sequence effect estimates to inform breeding decisions in multiple contexts. Other statistical approaches to calculate breeding values are known to those skilled in the art and can be used in substitution without departing from the spirit and scope of this invention.

Further, methods for determining the statistical significance of a correlation between a phenotype and a genotype, in this case a nucleic acid sequence, may be determined by any statistical test known in the art and with any accepted threshold of statistical significance being required. The application of particular methods and thresholds of significance are well within the skill of the ordinary practitioner of the art.

Nucleic acid sequence effect estimates and/or breeding values for one or more traits of interest provide the basis for determining one or more nucleic acid sequences of interest in comparisons of two or more nucleic acid sequences. With this a priori information, breeding selections are conducted on a nucleic acid sequence, rather than marker, basis, wherein a first plant is crossed with a second plant that contains at least one locus where the nucleic acid sequence of the second plant is different from the first plant nucleic acid sequence; and at least one progeny plant is selected by detecting the nucleic acid sequence or set of nucleic acid sequences of the first plant, wherein the progeny plant comprises in its genome one or more nucleic acid sequences of interest of the first plant and at least one nucleic acid sequence of interest of the second plant; and the progeny plant is used in activities related to germplasm improvement, herein defined as including using the plant for line and variety development, hybrid development, transgenic event selection, making breeding crosses, testing and advancing a plant through self fertilization, purification of lines or sub-lines, using plant or parts thereof for transformation, using plants or parts thereof for candidates for expression constructs, and using plant or parts thereof for mutagenesis.

In one aspect, this invention provides high throughput sequencing to identify large segments of nucleic acids, in one or more regions of a plant genome, that provide a basis to compare two or more germplasm entries. These regions of contiguous nucleic acid sequence are indicative of the conservation of genetic identity of all intervening genes from a common progenitor. In cases where conserved sequence segments are coincident with segments in which QTL have been identified it is possible to deduce with high probability that QTL inferences can be extrapolated to other germplasm having an identical sequence in that locus. This a priori information provides the basis to select for favorable QTLs prior to QTL mapping within a given population. For example, plant breeding decisions could comprise:

a) Selection among new breeding populations to determine which populations have the highest frequency of favorable nucleic acid sequences, wherein sequences are designated as favorable based on coincidence with previous QTL mapping; or b) Selection of progeny containing said favorable nucleic acid sequences in breeding populations prior to, or in substitution for, QTL mapping within that population, wherein selection could be done at any stage of breeding and could also be used to drive multiple generations of recurrent selection; or c) Prediction of progeny performance for specific breeding crosses; or d) Selection of lines for germplasm improvement activities based on said favorable haplotypes, including line development, hybrid development, selection among transgenic events based on the breeding value of the haplotype that the transgene was inserted into, making breeding crosses, testing and advancing a plant through self fertilization, using plant or parts thereof for transformation, using plants or parts thereof for candidates for expression constructs, and using plant or parts thereof for mutagenesis.

An additional unique aspect of this invention is the ability to select for specific genes or gene alleles, as they are targeted by high throughput sequencing. For example, in cases where the nucleic acid sequence is coincident with segments in which genes have been identified it is possible to deduce with high probability that gene inferences can be extrapolated to other germplasm having an identical genotype in that locus. This a priori information provides the basis to select for favorable genes or gene alleles on the basis of nucleic acid sequencing within a given population.

For example, plant breeding decisions could comprise:
  a) Selection among new breeding populations to determine which populations have the highest frequency of favorable nucleic acid sequences, wherein sequences are designated as favorable based on coincidence with previous gene mapping; or
  b) Selection of progeny containing said favorable nucleic acid sequences in breeding populations, wherein selection is effectively enabled at the gene level, wherein selection could be done at any stage of inbreeding and could also be used to drive multiple generations of recurrent selection; or
  c) Prediction of progeny performance for specific breeding crosses; or
  d) Selection of lines for germplasm improvement activities based on said favorable haplotypes, including line development, hybrid development, selection among transgenic events based on the breeding value of the haplotype that the transgene was inserted into, making breeding crosses, testing and advancing a plant through self fertilization, using plant or parts thereof for transformation, using plants or parts thereof for candidates for expression constructs, and using plant or parts thereof for mutagenesis.

Further, in another preferred embodiment of this invention, the a priori information on the frequency of favorable nucleic acid sequences in breeding populations enables pre-selection. That is, parental lines are selected based on the historical genotype-phenotype association information for the purpose of driving favorable nucleic acid frequency for multiple traits simultaneously. In pre-selection, breeders can predict the phenotypic contribution for multiple traits of any line based on that line's fingerprint information, which corresponds to a composition of pre-defined sequences. This multi-trait sequence selection approach economizes a breeding program by initiating selection at the initial stage of choosing parental crosses and it also reduces the need for costly, time-consuming phenotyping of progeny.

A preferred sequence provides a preferred property to a parent plant and to the progeny of the parent when selected by a marker means or phenotypic means. The method of the present invention provides for selection of preferred sequences, or sequences of interest, and the accumulation of these sequences in a breeding population.

In another embodiment, this invention enables indirect selection through selection decisions for at least one nucleic acid sequence based on at least one nucleic acid sequence effect estimate such that additional phenotypes are indirectly selected upon due to the additional nucleic acid sequence effect estimates for other phenotypic traits.

Another preferred embodiment of the present invention is to build additional value by selecting a composition of nucleic acid sequences wherein each sequence has an estimated associated phenotype that is not negative with respect to yield, or is not positive with respect to maturity, or is null with respect to maturity, or amongst the best 50 percent with respect an agronomic trait, transgene, and/or a multiple trait index when compared to any other nucleic acid sequence at the same locus in a set of germplasm, or amongst the best 50 percent with respect to an agronomic trait, transgene, and/or a multiple trait index when compared to any other loci across the entire genome in a set of germplasm, or the nucleic acid sequence being present with a frequency of 75 percent or more in a breeding population or a set of germplasm can be taken as evidence of its high value, or any combination of these.

This invention anticipates a stacking of nucleic acid sequences from at least two loci into plants or lines by crossing parent plants or lines containing different nucleic acid sequences, that is, different genotypes. The value of the plant or line comprising in its genome stacked nucleic acid sequences from two or more loci can be estimated by a composite breeding value, which depends on a combination of the value of the traits and the value of the nucleic acid sequence(s) to which the traits are linked. The present invention further anticipates that the composite breeding value of a plant or line can be improved by modifying the components of one or each of the nucleic acid sequences. Additionally, the present invention anticipates that additional value can be built into the composite breeding value of a plant or line by selection of at least one recipient nucleic acid sequence with a preferred nucleic acid sequence effect estimate or, in conjunction with the frequency of said nucleic acid sequence in the germplasm pool, breeding value to which one or any of the other nucleic acid sequences are linked, or by selection of plants or lines for stacking two or more nucleic acid sequences from two or more loci by breeding.

Another embodiment of this invention is a method for enhancing breeding populations by accumulation of one or more nucleic acid sequences in one or more loci, in a germplasm. Loci include genetic information and provide phenotypic traits to the plant. Variations in the genetic information can result in variation of the phenotypic trait and the value of the phenotype can be measured. The genetic mapping of the nucleic acid sequences allows for a determination of linkage across sequences. The nucleic acid sequence of interest is novel in the genome of the progeny plant and can in itself serve as a genetic marker of a locus of interest. Notably, this nucleic acid sequence can also be used as an identifier for a gene or QTL. For example, in the event of multiple traits or trait effects associated with the nucleic acid sequence, only one marker would be necessary for selection purposes. Additionally, the locus of interest may provide a means to select for plants that have the linked locus.

In another embodiment, at least one preferred nucleic acid of the present invention is stacked with at least one transgene. In another aspect, at least one transgenic event is advanced based on linkage with or insertion in a preferred nucleic acid, as disclosed in published U.S. Patent Application US 2006/0282911, which is incorporated herein by reference in its entirety.

In still another embodiment, the present invention acknowledges that preferred nucleic acids identified by the methods presented herein may be advanced as candidate genes for inclusion in expression constructs, i.e., transgenes. Nucleic acids of interest may be expressed in plant cells by operably linking them to a promoter functional in plants. In another aspect, nucleic acids of interest may have their expression modified by double-stranded RNA-mediated gene suppression, also known as RNA interference s ("RNAi"), which includes suppression mediated by small interfering RNAs ("siRNA"), trans-acting small interfering RNAs ("ta-siRNA"), or microRNAs ("miRNA"). Examples of RNAi methodology suitable for use in plants are described in detail in U.S. patent application publications 2006/0200878 and 2007/0011775.

Methods are known in the art for assembling and introducing constructs into a cell in such a manner that the nucleic acid molecule for a trait is transcribed into a functional mRNA molecule that is translated and expressed as a protein product. For the practice of the present invention, conventional compositions and methods for preparing and using constructs and host cells are well known to one skilled in the art, see for example, Molecular Cloning: A Laboratory Manual, 3rd edition Volumes 1, 2, and 3 (2000) J. F. Sambrook, D. W. Russell, and N. Irwin, Cold Spring Harbor Laboratory Press. Methods for making transformation constructs particularly suited to plant transformation include, without limitation, those described in U.S. Pat. Nos. 4,971,908, 4,940,835, 4,769,061 and 4,757,011, all of which are herein incorporated by reference in their entirety. Transformation methods for the introduction of expression units into plants are known in the art and include electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; protoplast transformation as illustrated in U.S. Pat. No. 5,508,184; and *Agrobacterium*-mediated transformation as illustrated in U.S. Pat. Nos. 5,635,055; 5,824,877; 5,591,616; 5,981,840; and 6,384,301.

The present invention also provides for the screening of progeny plants' loci of interest and using the nucleic acid effect estimate as the basis for selection for use in a breeding program to enhance the accumulation of preferred nucleic acid sequences.

Using this method, the present invention contemplates that nucleic acid sequences of interest are selected from a large population of plants. Additionally, these nucleic acid sequences can be used in the described breeding methods to accumulate other beneficial and preferred loci and maintain these in a breeding population to enhance the overall germplasm of the plant. Plants considered for use in the method include but are not limited to, corn, soybean, cotton, wheat, rice, canola, oilseed rape, sugar beet, *sorghum*, millet, alfalfa, forage crops, oilseed crops, grain crops, fruit crops, ornamental plants, vegetable crops, fiber crops, spice crops, nut crops, turf crops, sugar crops, beverage crops, tuber crops, root crops, and forest crops.

In summary, this invention describes the novel combination of high throughput sequencing and molecular breeding methodologies to enable the use of direct nucleic acid sequence information to carry out molecular plant breeding. The invention also includes means to selectively target polymorphic nucleotide sites and to DNA tag samples prior to sequence determination. Taken together, this invention enables the plant breeder to use sequence information in parent selection, progeny selection, choosing tester combinations, developing pedigrees, fingerprinting samples, screening for haplotype diversity, and for building databases of sequence associations to trait and performance data.

EXAMPLES

Example 1. Sequence Directed Selection

An important aim of any breeding program is to incorporate economically or otherwise important traits into a breeding line or population. The ability to directly determine the sequence of region linked to the trait or to directly determine the sequence(s) of the loci which are causative to the trait will allow the breeder to determine which individuals or lines in a population likely exhibit the trait of interest and thus inform advancement decisions. A sample workflow for high throughput sequencing is depicted in FIG. 1. The present example demonstrates a method of the invention for making sequence-directed selection. The method is differentiated from traditional marker-assisted selection in that it uses direct nucleic acid sequence information for selection instead of a marker.

Low linolenic acid soybean oil is of commercial interest because it does not result in trans fats during processing and use and therefore is healthier for human consumption. A gene that is essential for linolenic acid biosynthesis is the fad3 gene. In soybeans, there are at least three fad3 genes and mutations in two of the genes, fad3b and fad3c, can result in low linolenic acid. Exemplary primers and probes for the detection of mutations in these genes are set forth in published U.S. Patent Application 20060107348, which is incorporated herein by reference in its entirety.

Figure 2:
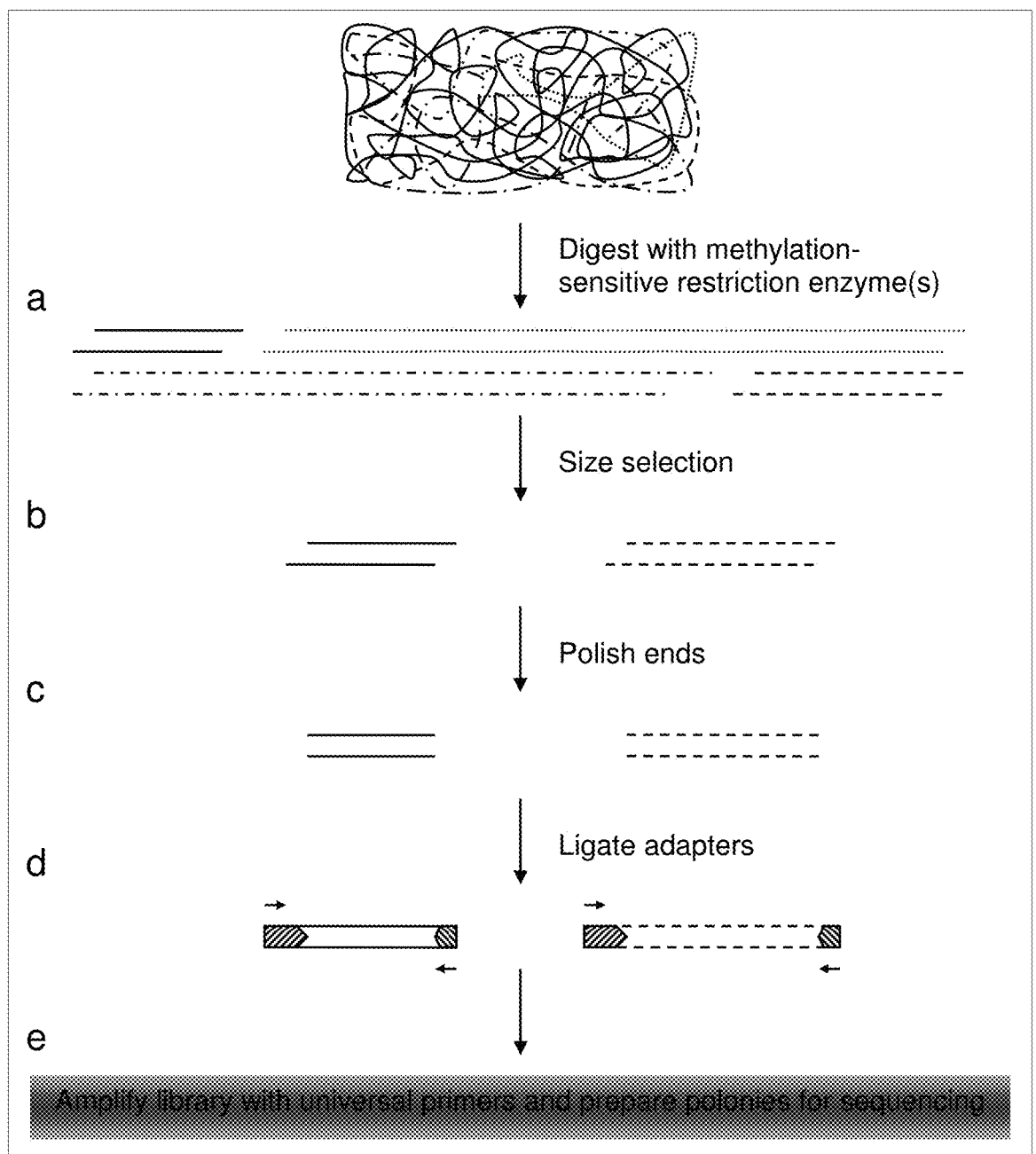
FIG. 2 illustrates a method for reducing complexity of template nucleic acids from selective digestion.
Figure 3:
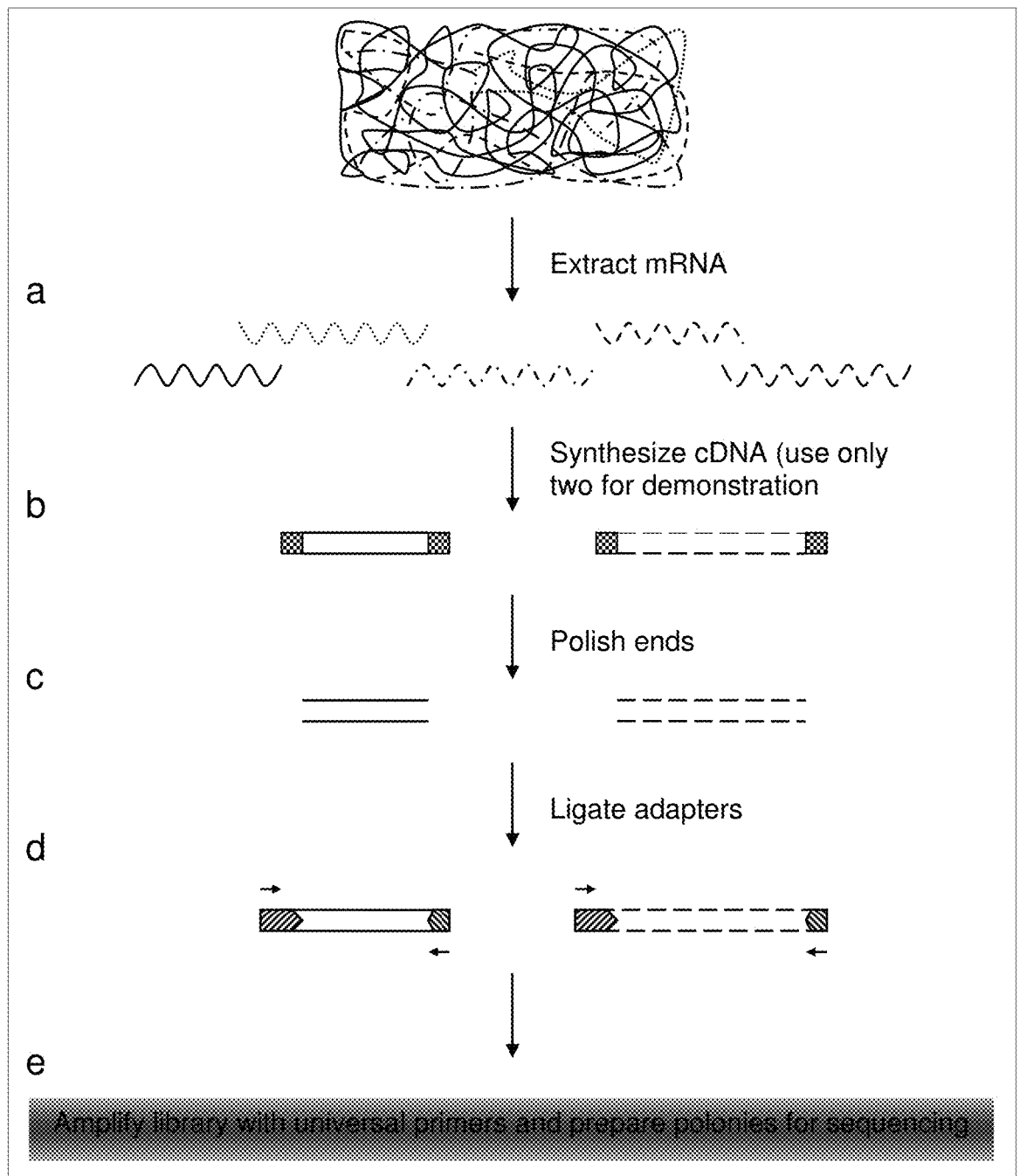
FIG. 3 illustrates a method for targeted complexity reduction from the transcriptome.
Figure 4:
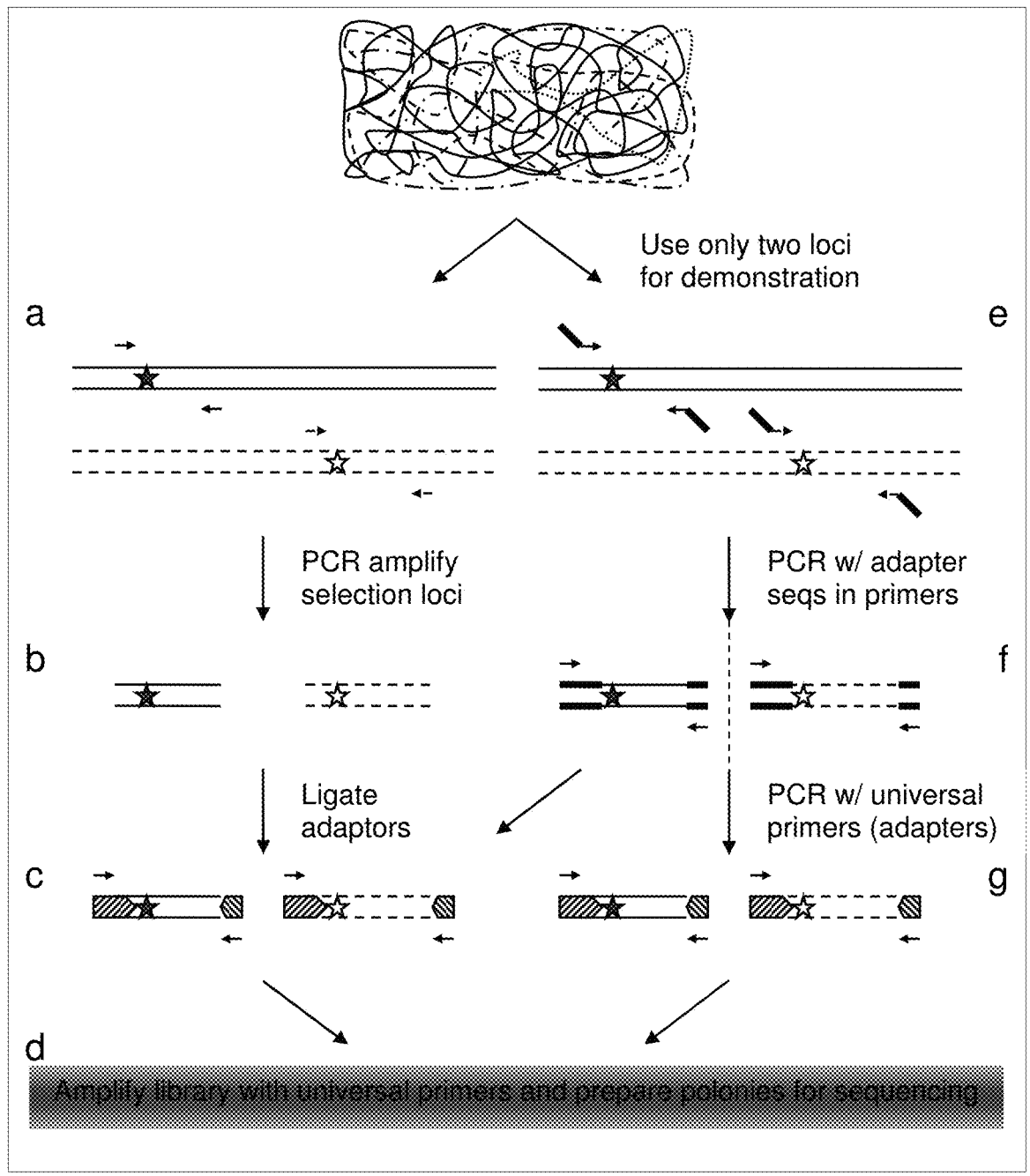
FIG. 4 illustrates a method for targeted complexity reduction by amplification of at least one genomic region of interest.
Figure 5:
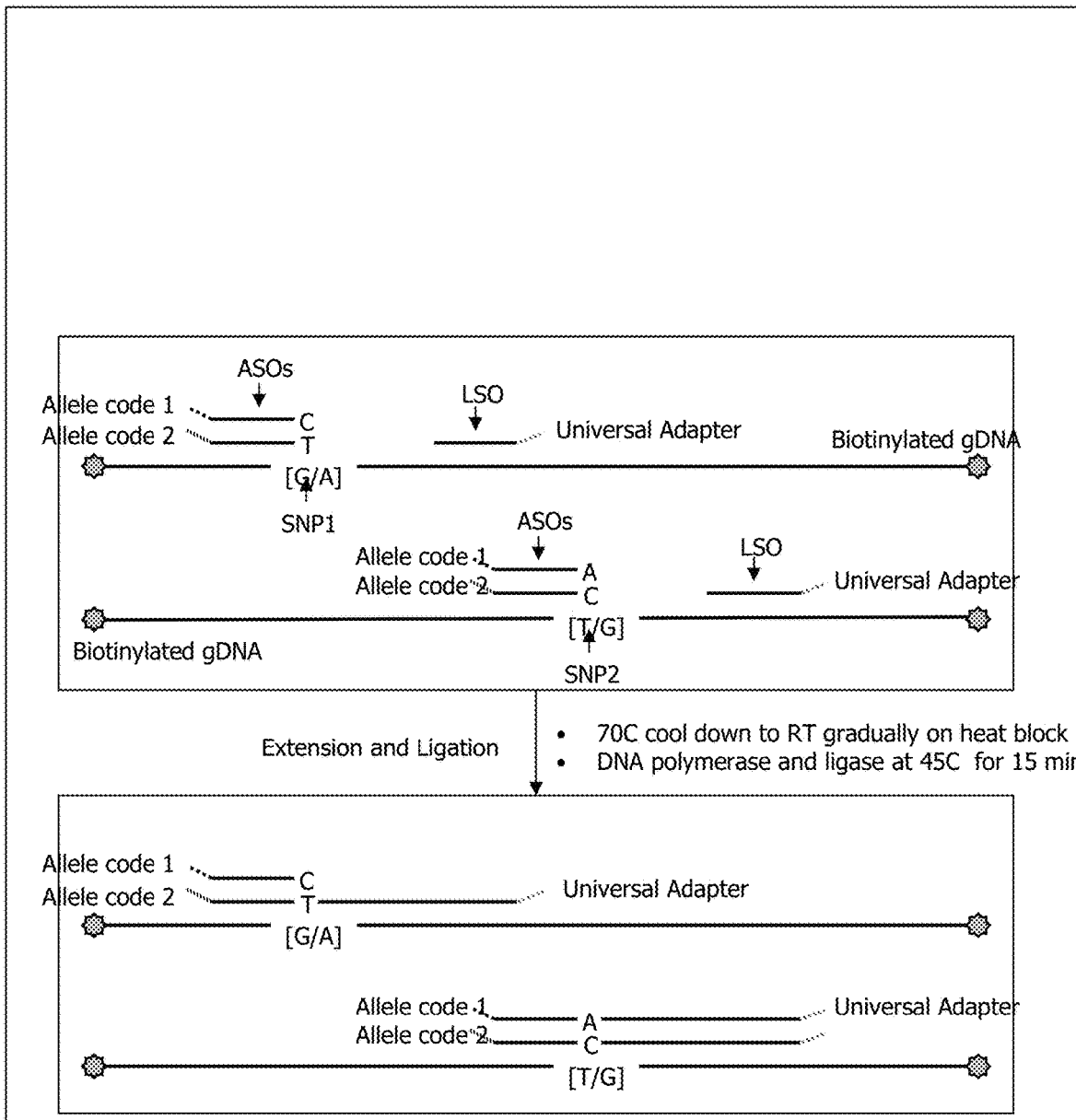
FIG. 5 illustrates a method for targeted complexity reduction, including sample tagging, by allele specific extension/ligation.
Figure 6:
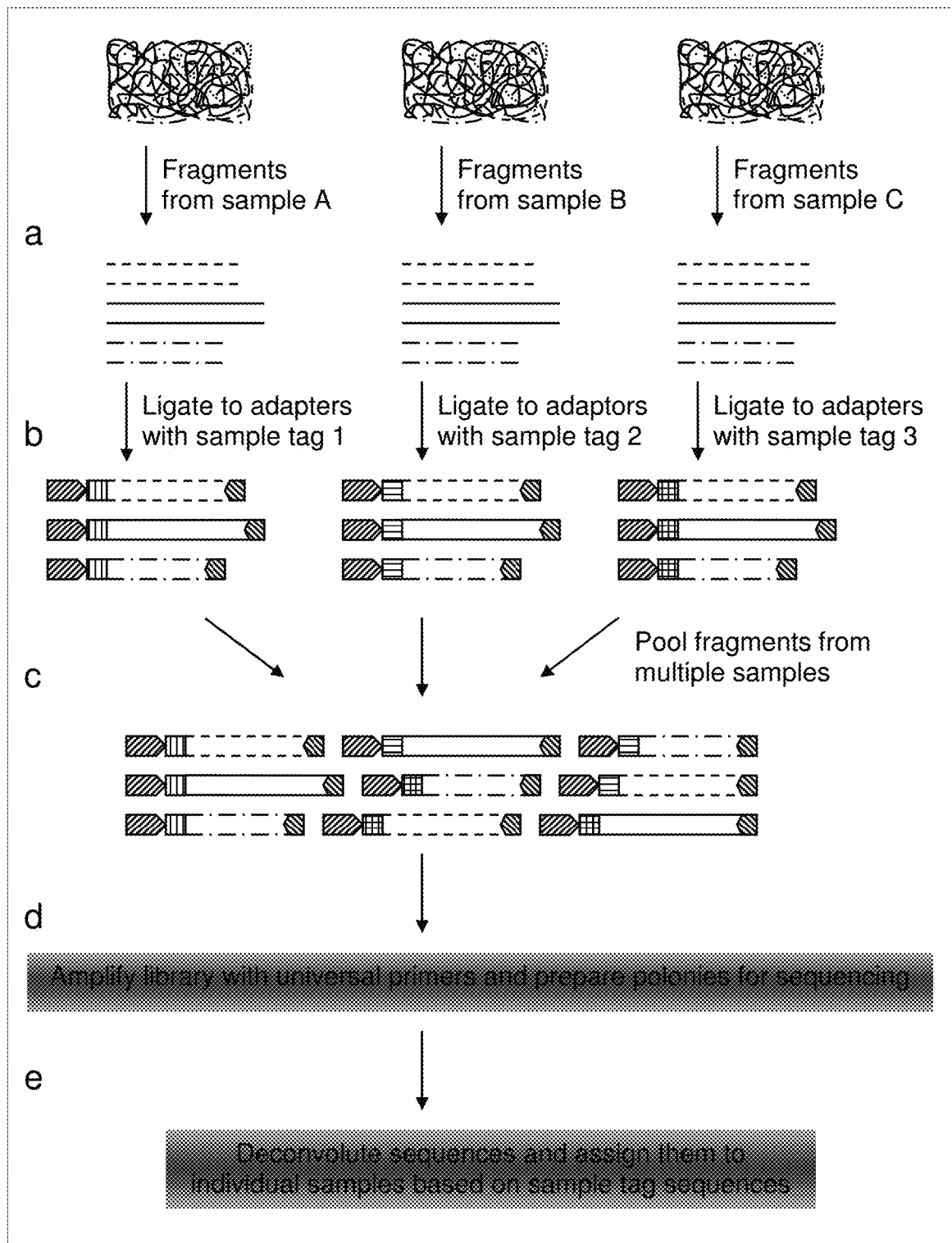
FIG. 6 illustrates a method for the multiplexing of samples using DNA tags attached to the template nucleic acids through ligation.

In one aspect, a first step for sequence-directed selection can be genome complexity reduction, wherein different strategies are exemplified in FIGS. 2-5. That is, a reduced representation library can be obtained by selective digestion and purification, using enzymes known in the art (FIG. 2). In other aspects, the library can be targeted from the transcriptome (FIG. 3). In still other aspects, SNP-containing regions are isolated using allele-specific extension/ligation (FIG. 5).

In still other aspects, the sequence-targeted genomic regions are selectively amplified (FIG. 4). In the present example, the Fad3c indel region was amplified using specific primers for insertion and deletion. This method is useful when the region of interest comprises an indel and is especially useful in screening for transgenes. Alternatively, the region spanning the nucleic acid of interest is amplified. In the present example, a second complexity reduction strategy was employed, wherein the SNP assay for the Fad3b region was used to amplify the region containing the SNP for the purpose of sequencing. In general, this approach is especially useful for leveraging existing SNP PCR-based assay libraries and using the known primer sets as a tool in complexity reduction. The present invention anticipates using SNPs provided by published U.S. Patent Applications US 2005/0204780, US 2005/0216545, US 2005/0218305, and US 2006/0504538, as both targets for sequencing as well as for use in genome complexity reduction as described herein.

A second step that can be useful for sequence-directed selection is use of DNA tags in order to enable sample multiplexing. In the present example, each sample in a multiplex set was assigned a unique DNA tag, i.e., a sequence tag differing by at least one base pair from the other barcodes in the set. In a preferred aspect, the percentage of G and C bases is balanced to minimize bias in the sequencing process. The DNA tag can range in length from about 2 to about 20 bp. In the present examples, with 384 PCR samples, representing 192 germplasm entries assayed for both the Fad3b SNP and Fad3c indel, 6 bp sequences were used and each sample was sequenced for both the SNP and the indel regions.

Figure 7:
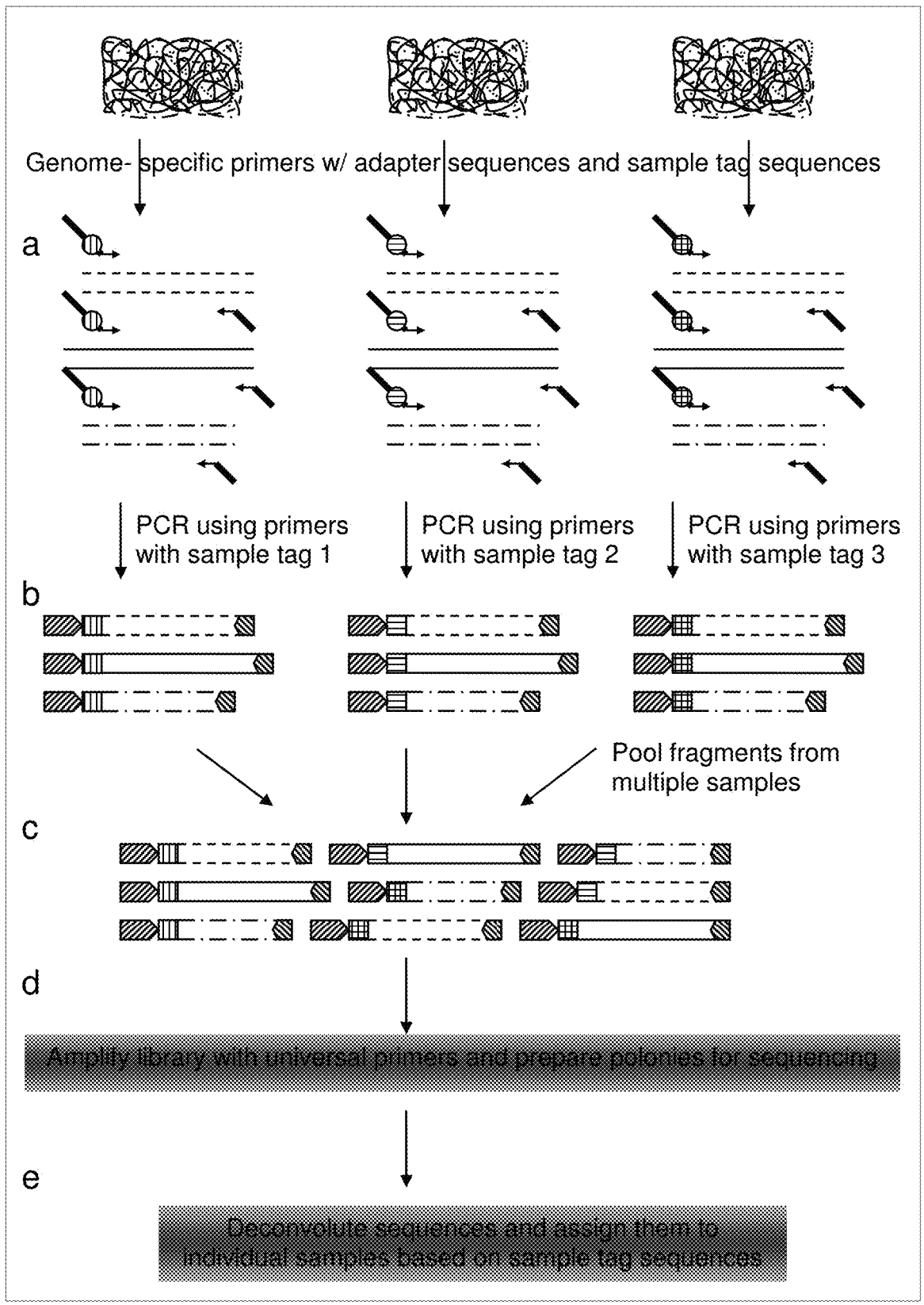
FIG. 7 illustrates a method for the multiplexing of samples using DNA tags attached to the template nucleic acids through PCR.
Figure 8:
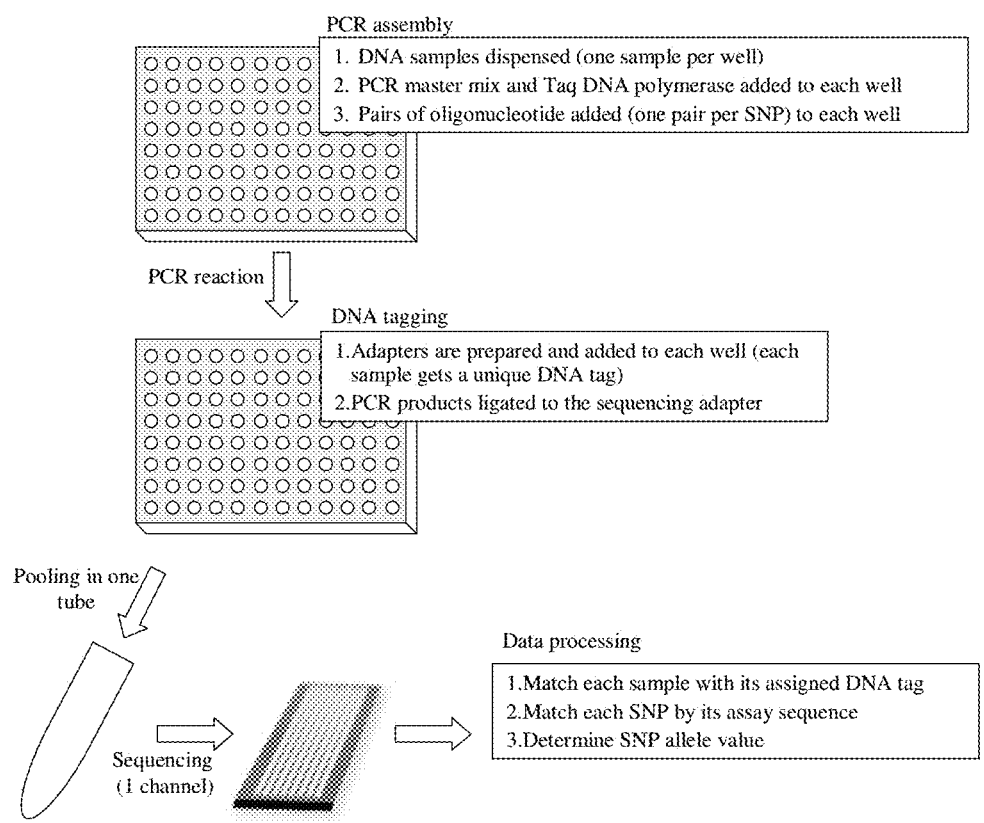
FIG. 8 illustrates a workflow for high throughput nucleic acid sequencing.
Figure 9:
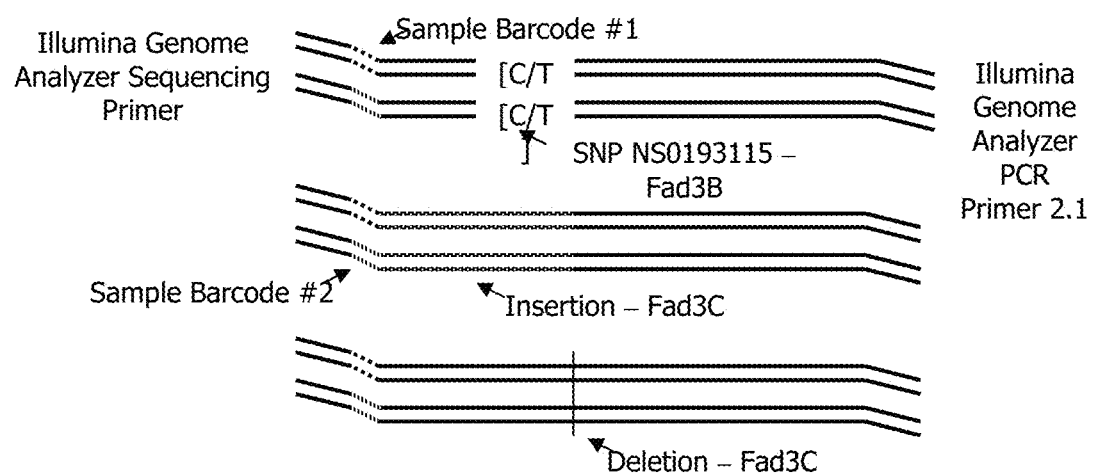
FIG. 9 illustrates a method for preparing samples for sequence directed selection for a SNP and an indel.

In one aspect, the DNA tags are added to the PCR primers as shown in FIG. 7. Alternatively, they can be incorporated into allele-specific extension/ligation as shown in FIG. 5, with the barcode ligated to the allele-specific extension/ligation products or added to the products using PCR. In the present example, the DNA tags were included in the PCR primers. FIG. 9 illustrates a schematic of the resulting template that will be used for sequencing, showing both the Fad3b SNP and the Fad3c indel. Specifically, a pair of oligonucleotides were synthesized to aid in the sequence determination for the fad3b locus. A forward oligonucleotide primer is synthesized to include a 6-nucleotide DNA tag (Table 1) and a sequence that matches the nucleotide sequence that is 5' to the fad3b mutation which is known to affect gene function. For the purposes of this invention, a mutation is the same as a polymorphic nucleotide and represents a polymorphic locus. A reverse oligonucleotide primer is synthesized to a sequence complementary to the region 3' of the fad3a mutation. A second pair of forward and reverse PCR primers are generated in the similar fashion to match a mutation which deletes the fad3c gene which is also known to reduce linolenic acid in soybean oil. Since the deletion extends beyond the boundaries of the fad3 gene, one pair of primers is designed within the genes coding region to determine the sequence of the fad3c gene if the gene is present and a second set of primers is designed to span the deletion of the fad3c locus, if the gene is absent. The distance between the nucleotide pairs is designed to be between 10 and 200 nucleotides and the mutation adjacent to the end of the forward primer, therefore in close proximity to the DNA tag. The more similar the distance between the primers, the more likely the PCR amplification of the template will be unbiased across the multiple loci, however, longer distances can be required in some examples to find stretches of nucleotides appropriate for robust primer design, e.g. devoid of repetitive sequences, non-existent sequence structure and balanced GC content. The same DNA tag can be used for the forward primer in the three pairs of primers. The three pairs represented a genotyping or fingerprinting set which can be used for one sample.

TABLE 1

Exemplary 6 nucleotide DNA tags for the 192 soybean varieties genotyped in the present example.

| W | Code |
|---|---|
| 1 | AACGCT |
| 2 | AACGTC |
| 3 | AACTCG |
| 4 | AAGACC |
| 5 | AAGGGT |
| 6 | AAGTGC |
| 7 | ACACGA |
| 8 | ACACTG |
| 9 | ACAGGT |
| 10 | ACATCG |
| 11 | ACCAAC |
| 12 | ACCACT |
| 13 | ACCATG |
| 14 | ACCCTA |
| 15 | ACCGAA |
| 16 | ACCGTT |
| 17 | ACCTTC |
| 18 | ACGAGA |
| 19 | ACGCTT |
| 20 | ACGGAT |
| 21 | ACGTGT |
| 22 | ACTACC |
| 23 | ACTCCA |
| 24 | ACTCTC |
| 25 | ACTGAC |
| 26 | ACTGCT |
| 27 | AGAACG |
| 28 | AGACAC |
| 29 | AGAGAG |
| 30 | AGCGTA |
| 31 | AGCTAG |
| 32 | AGCTGT |
| 33 | AGGAAG |
| 34 | AGGAGT |
| 35 | AGGTCA |
| 36 | AGTCGT |
| 37 | ATCACG |
| 38 | ATCCAC |
| 39 | ATCCCA |
| 40 | ATCGGT |
| 41 | ATCTGC |
| 42 | ATGAGG |
| 43 | ATGCCT |
| 44 | ATGCTG |
| 45 | ATGGAG |
| 46 | ATGGCA |
| 47 | ATGTCG |
| 48 | ATTGCG |
| 49 | CAATGG |
| 50 | CAGAGT |
| 51 | CAGATG |
| 52 | CAGCTT |
| 53 | CAGTAG |
| 54 | CAGTTC |
| 55 | CATAGG |
| 56 | CATTCG |

TABLE 1-continued

Exemplary 6 nucleotide DNA tags for the 192 soybean varieties genotyped in the present example.

| W | Code |
|---|---|
| 57 | CCAAGT |
| 58 | CCACTT |
| 59 | CCATAG |
| 60 | CCATGA |
| 61 | CCATTC |
| 62 | CCGATA |
| 63 | CCGTAA |
| 64 | CCTATC |
| 65 | CCTCTA |
| 66 | CCTGAT |
| 67 | CGAAAG |
| 68 | CGAAGA |
| 69 | CGAATC |
| 70 | CGACAT |
| 71 | CGCATT |
| 72 | CGGAAT |
| 73 | CGTATG |
| 74 | CGTCTT |
| 75 | CGTTCT |
| 76 | CGTTTC |
| 77 | CTAAGG |
| 78 | CTACTG |
| 79 | CTAGCA |
| 80 | CTAGGT |
| 81 | CTAGTC |
| 82 | CTATCG |
| 83 | CTCAGT |
| 84 | CTCATG |
| 85 | CTCGTA |
| 86 | CTCTCT |
| 87 | CTCTGA |
| 88 | CTGACA |
| 89 | CTGGAA |
| 90 | CTTACG |
| 91 | CTTCCA |
| 92 | CTTGAC |
| 93 | CTTGCT |
| 94 | CTTTCC |
| 95 | GAAGCT |
| 96 | GAAGTC |
| 97 | GAATGC |
| 98 | GACACA |
| 99 | GACATC |
| 100 | GACGTA |
| 101 | GACTAG |
| 102 | GACTCT |
| 103 | GACTGA |
| 104 | GAGACT |
| 105 | GAGGTT |
| 106 | GATAGC |
| 107 | GATCGT |
| 108 | GATGAG |
| 109 | GATGGA |
| 110 | GATTGG |
| 111 | GCAGAT |
| 112 | GCATGT |
| 113 | GCCATA |
| 114 | GCCTAA |
| 115 | GCTAAG |
| 116 | GCTAGA |
| 117 | GCTCTT |
| 118 | GCTGTA |
| 119 | GCTTCT |
| 120 | GCTTTG |
| 121 | GGAACA |
| 122 | GGAATG |
| 123 | GGAGTA |
| 124 | GGCTAT |
| 125 | GGCTTA |
| 126 | GGTCAA |
| 127 | GGTTAG |
| 128 | GGTTCA |
| 129 | GTACCA |
| 130 | GTAGAC |

TABLE 1-continued

Exemplary 6 nucleotide DNA tags for the 192 soybean varieties genotyped in the present example.

| W | Code |
|---|---|
| 131 | GTAGGA |
| 132 | GTCAAG |
| 133 | GTCCAA |
| 134 | GTCGAT |
| 135 | GTCTAC |
| 136 | GTCTCA |
| 137 | GTCTGT |
| 138 | GTGAGA |
| 139 | GTGCTA |
| 140 | GTGTTG |
| 141 | GTTACC |
| 142 | GTTCAG |
| 143 | GTTCCT |
| 144 | GTTTCG |
| 145 | TACAGC |
| 146 | TACCTC |
| 147 | TACGAG |
| 148 | TAGCTG |
| 149 | TAGTCG |
| 150 | TCAAGC |
| 151 | TCACCA |
| 152 | TCACTC |
| 153 | TCAGTG |
| 154 | TCATGG |
| 155 | TCCAGT |
| 156 | TCCCTT |
| 157 | TCGACA |
| 158 | TCGATC |
| 159 | TCGCAA |
| 160 | TCGTAC |
| 161 | TCGTGA |
| 162 | TCGTTG |
| 163 | TCTGGA |
| 164 | TCTTCC |
| 165 | TGAAGG |
| 166 | TGAGCA |
| 167 | TGAGTC |
| 168 | TGCAAG |
| 169 | TGCATC |
| 170 | TGCGAA |
| 171 | TGCGTT |
| 172 | TGCTAC |
| 173 | TGCTGA |
| 174 | TGGAAC |
| 175 | TGGATG |
| 176 | TGGCAT |
| 177 | TGGTCT |
| 178 | TGTACC |
| 179 | TGTCAG |
| 180 | TGTCGA |
| 181 | TGTCTC |
| 182 | TGTGAC |
| 183 | TGTGCT |
| 184 | TGTGTG |
| 185 | TGTTCG |
| 186 | TGTTGC |
| 187 | TTCAGG |
| 188 | TTCGCT |
| 189 | TTCGTG |
| 190 | TTCTCC |
| 191 | TTGACG |
| 192 | TTGCAC |

An additional 192 genotyping sets were then generated where each set is identical except that the DNA tag in the forward primer of the three pairs of oligonucleotides is exchanged for a unique tag from the list of 4096 possible tags. The sequences of the fad3b and fad3c mutations were then determined for a population of 192 soybean varieties in the following manner. A single seed from each of the 192 lines was sampled to remove a portion of seed tissue while maintaining seed viability as described, for example, in US 2006/0046264 and US 2007/0204366, each of which is incorporated herein by reference.

To prepare template for sequencing, DNA was prepared for each of the tissue samples and then 10 ng was dispensed into 2, 96 well microtitre plates. To each well, a PCR master mix was added along with Taq polymerase, according to manufacturer's recommendations (Roche, ABI). Finally, 100 µM of a selected genotyping primer set, including matching DNA tags, was added to each well. The plate was heated to 95° C. for nine minutes to denature the DNA.

Twenty cycles of PCR were then completed using the following conditions: 94° C. for 30 sec, 55° C. for 30 sec, 72° C. for 2 min, followed by a final 10 minute extension at 72° C.

After PCR, all 192 lines were combined into a single well which was then used for a HT sequencing reaction, according to the manufacturer's directions (Illumina Genome Analyzer). Briefly, equal amounts of the 384 PCR products were mixed and subsequently purified using PCR purification methods known in the art. Approximately 5-10 ng of the purified template was amplified with enrich PCR per Illumina Genome Analyzer specifications. The enrich PCR also adds the adapter required for the downstream bridge PCR reaction if the adapters were not already incorporated in the primers. The enrich PCR product is purified, again using PCR purification methods known in the art, and the resulting template is sequencing per Illumina Genome Analyzer specifications.

Figure 10:
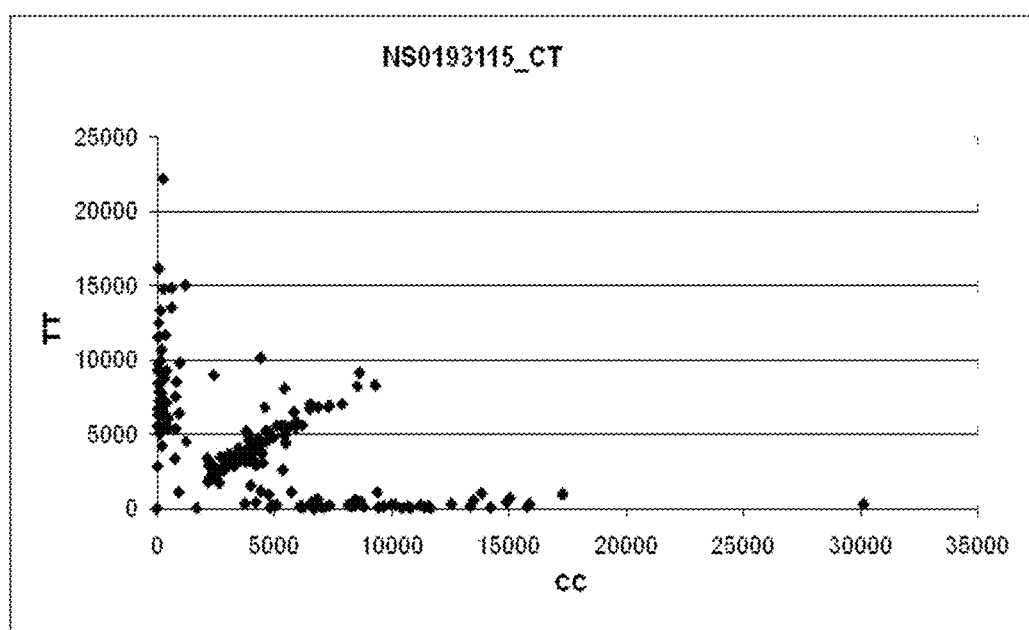
FIG. 10 is a scatter plot for results of genotyping for the purpose of sequence-directed selection using high throughput sequencing for the Fad3b SNP as described in Example 1.
Figure 11:
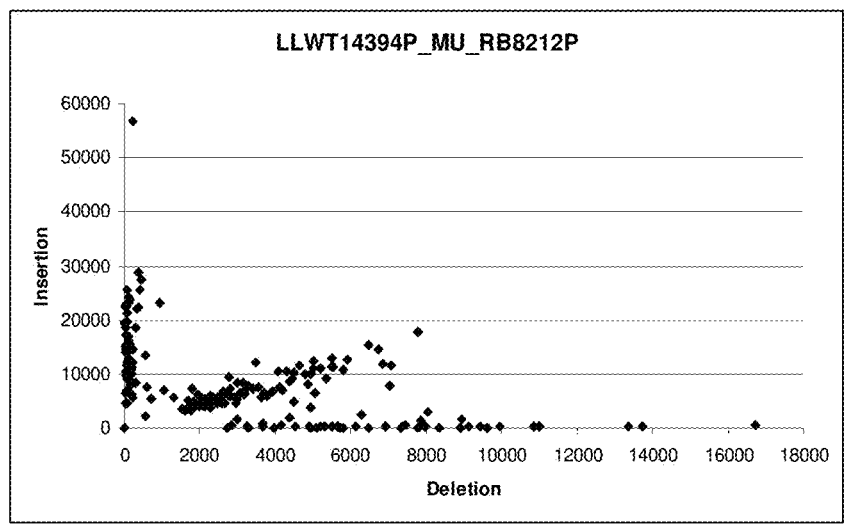
FIG. 11 is a scatter plot for results of genotyping for the purpose of sequence-directed selection using high throughput sequencing for the Fad3c indel as described in Example 1.

The sequences obtained from the sequencing reaction were binned according to the DNA tag sequence. Within each bin, the sequences were analyzed by alignment to the SNP and indel forward primers in order to determine if the known mutation, any other variation or wild-type nucleotides were present next to the 3' complementary oligonucleotide. SNP genotypes were called based on the sequences at the SNP position (see FIG. 10 for resulting scatter plot). Indel genotypes were determined by the matches to the sequences of the two forward primers (see FIG. 11 for resulting scatter plot). Matching sequence counts can be plotted to handle backgrounds. Advanced scoring tools can be used/developed for normalization/calibration and more reliable genotype calls. If both mutant and wild type sequences were identified, the sample was predicted to be heterozygous. If only nucleotide sequences that corresponded to wild type sequences were present, then the sample was classified as normal linolenic acid. If known mutant sequences were identified, then the samples were classified as low linolenic acid. Identifying and classifying the sequences at the fad3b locus, the fad3c locus and at the fad3c deletion locus allows a breeder to screen plants to characterize the low linolenic acid-associated genotype and then decide which low linolenic acid varieties to advance to yield testing.

Example 2. Sequence-Directed Introgression

A powerful tool in plant breeding is back-crossing. Back-crossing allows a breeder to extract one or more of the best characteristics in a donor line and systematically introgress them into a recurrent parent line. In essence, the genomic region(s) at one or more selected donor DNA loci are systematically introgressed into a recurrent parent genome, replacing the nucleic acids at the corresponding loci in the recurrent parent genome. The types of characteristics that are typically introgressed between lines include, but are not limited too, transgenes, disease resistance, pest resistance, quality traits, agronomic traits, etc. Traditionally, this process can take five or more generations to obtain the traits of interest in a progeny that also shows equivalency to the recurrent parent and has the recurrent parent's agronomic performance. If the performance of the converted line does not equal the predicted performance of the recurrent parent plus the new trait, it can often be very difficult to understand the issue and how to correct.

Sequence directed back-crossing (SDBC) can greatly accelerate the process and result in a more quantifiable outcome. Using sequences, the progeny from each back-cross generation are examined for both the nucleic acid sequences of the donor parent that encode or are linked to the characteristics of interest and nucleic sequences in the recurrent parent genome. The examination takes into account both differences (polymorphisms) and identity between the sequences. Back-cross progeny are selected and advanced based on their nucleic acid sequence composition, which includes both the nucleic acid sequences encoding or linked to the target trait and the highest percent of nucleic acid sequences matching the recurrent parent sequence. By directing the process with sequence rather than marker information, the process can be completed in fewer generations, with a higher recovery of the recurrent parent.

A particular example of SDBC is the directed introgression of a transgene from a donor line to a recurrent parent line and an example of a transgene encodes resistance to the herbicide, also known as the bacterial CP4 gene, which is a critical part of the sequence required for the Roundup Ready® trait. In this example, a donor line is fixed or homozygous for the CP4 gene and it is desirable to introgress the CP4 into a recurrent parent line. The breeder planted 15 seeds of recurrent parent in a row next to a row of 15 seeds of the CP4 donor parent. Four crosses are made by pollinating the donor ears with pollen from the recurrent parent. The resulting seed is the F1 seed. A triplet is planted with a recurrent parent row planted between two rows of F1 seed obtained from the one or two best looking F1 ears. At the time of pollen shed, the recurrent parent is used to pollinate 4 F1's in each of the flanking rows (8 total crosses). The best two BC1 ears are harvested from each row and the BC1 seed is bulked. On average, it is expected that the BC1 seed would contain 25% of the donor genome and 75% of the recurrent parent genome, however, the exact content of any one individual plant would vary within a normal distribution. Subsequent back crossing efforts would be enhanced by selecting the subset of seeds with the highest recurrent parent genome and which contain the transgene. The BC1 seed would also be segregating for the CP4 transgene. Sequencing is used to identify which of 93 BC1 plants had the highest amount of recurrent parent nucleic acid sequences and contained the transgene. The desirable subset can be identified by inspecting the sequence at a number of loci, for example 96, where one of the loci is the CP4 locus.

Seed from each of the parents, the F1 bulk and from each of 93 BC1 is planted in rows and plants cultivated. At the V4 stage ($4^{th}$ leaf stage), a leaf tear is taken from each plant and placed in a single well of a 96 well block. The DNA is prepped according to the method described in Dellaporta et al., 1983 Plant Mol Biol Rep 1: 19-21, which is incorporated by reference herein in its entirety. The DNA from each of the 96 loci are further prepared using an initial amplification. In this example, amplification is used to incorporate the DNA tag and adapters but other methods are known and applicable. A locus specific forward primer is designed which contained 18 nucleotides at the 3' end which would hybridize to the 5' of the target locus. The 5' end of the forward primer also contained 15 nucleotides which matched the 15 nucleotides 3' to a universal forward PCR primer. In the similar way, a reverse PCR primer is designed where 18 bases at the 3' end complemented the nucleotides 3' of the target locus. The reverse primer also contained 15 base pairs on the 5' end which matched the 3' end of a universal reverse primer. In this example, the target loci are 6-10 nucleotides, however they could range from just 2 nucleotides to several hundred or more. This process is repeated for each of the 96 loci where one of the loci is the CP4 locus. Ninety-five of the loci are selected to cover each arm of every chromosome and included a few extra markers flanking the CP4 locus.

In addition to the gene specific primers, universal primers are also designed. The forward universal primer is synthesized to contain the 15 nucleotides at the 5' end of the forward gene specific primer. The reverse universal primer is synthesized to hybridize to the universal PCR nucleotides on the reverse gene specific primer and in addition, contained a 5 nucleotide tag at the 5' end. Ninety-six (96) different universal reverse primers are synthesized with each primer containing a unique tag sequence chosen from the 1024 possible combinations provided by one of 4 bases at each of the 5 nucleotide positions. The samples are subject to PCR using standard conditions. The initial rounds of PCR have the objective of incorporating the universal primers and DNA tag in a limited number of copies of each locus. The 96 gene specific forward and reverse primer pairs are diluted and then combined to make a multiplexed, equimolar stock solution at a final concentration of 10 µmol total oligonucleotide per litre solution. PCR assays contained 1×PCR buffer, 2.5 mM $MgCl_2$, 0.2 mM dNTP mix, 1 U Taq DNA polymerase, 1 µM of the forward universal primer, 100 nM of the multiplexed primers and 1 µl of DNA extract. In addition, to each unique sample, a uniquely tagged reverse universal primer is added for a final concentration of 1 µM. Cycling is performed in an ABI 7900 with the following cycling program: Initial denaturation at 94° C. for 90 seconds; followed by 4 cycles of 94° C. for 30 seconds, 55° C. for 30 seconds and 72° C. for 30 seconds; followed by 22 cycles of 94° C. for 30 seconds and 72° C. for 60 seconds. The incorporation of the DNA tag through PCR or ligation is essential to the method, however, the subsequent amplification is not always necessary but can facilitate the downstream sample handling steps in preparation for sequencing. After PCR, 2 µl of amplification product is examined by agarose gel electrophoresis on 2% agarose gels subsequently stained with ethidium bromide to confirm the presence of a single product. Assays with a positive PCR reaction are combined into a single pool and purified using a Qiagen kit (Qiagen, USA). The purified products are then subjected to high throughput sequencing according to the manufacturer's protocol (Illumina Genome Analyzer 1G Analyzer, Illumina, Inc.). Two reads are obtained from each sequenced molecule. The first read is obtained by using a primer that corresponded to the forward universal PCR primer sequence. This sequencing primer resulted in a short read of the sequence at the locus for which the primer is designed and within a given sample, as identified by the tag. The tag is read using a short run from a sequencing primer designed to hybridize to the reverse universal primer sequence. This second sequence read is reinitiated after the read of the locus sequence is completed.

The sequences obtained from the sequencing reaction are binned according to the DNA tag sequence. This is done by trimming the second sequence read down to the DNA tag and then blasting the tags within one run to each other. Within each sample bin, the sequences are clustered to combine multiple reads of the same locus. The sequences at a given locus are then compared (using BLAST) to the expected sequence for the recurrent parent and the donor parent and the CP4 gene. If all the sequence reads matched the recurrent parent, the locus is designated as fixed for the recurrent parent. If the all the sequences matched the donor parent, the locus is fixed for the donor parent and one or more additional backcrosses would be needed to re-introduce the recurrent parent nucleic acids for that locus into the population. If both recurrent parent and donor parent sequences are observed, the locus is called heterozygous and the line could be selfed or further back-crossed to fix for the recurrent parent. This logic is followed for all 95 loci and for the CP4 locus. The progeny with the largest number of recurrent parent loci and which contained the CP4 locus are advanced to further back-crossing so as to further introgress and fix the recurrent parent nucleic acids at all the loci except for the donor nucleic acids at the CP4 locus.

The present invention further anticipates use of the methods described herein for introgression of 2 or more genomic regions, which may be transgenic or conventional (i.e, QTL).

Example 3. Molecular Fingerprinting Using HT Sequencing (Sequence Directed Fingerprinting)

Nucleotide sequences are ultimate assessment and measurement of genetic makeup of individual plants and genetic similarities among plant varieties/lines. Molecular fingerprints based on nucleotide profiles may provide general information across the genome that can be used, among other applications, to assess germplasm diversity, to help the selection of high performing parents and testers, to query new germplasm pools for potential introgression targets, to query new or existing germplasm pools for genomic regions associated with at least one phenotype of interest, as well as to protect germplasm intellectual properties. If two lines are sufficiently diverse, they are likely in different heterotic groups. That is, they can complement each other, and, when hybridized, have a high probability of generating a productive breeding cross or a hybrid combination. On the other hand, similarity among lines may suggest a potential suboptimal cross. Further, fingerprint similarity provides a basis for evaluation of intellectual property infringement.

Molecular fingerprints may focus on selected regions of the genome and reveal sequence information at specific loci including, but not limited to, those that are causative or linked to traits of economical importance. The presence or absence of particular nucleotide sequences or particular nucleotide sequence variants at one or more loci can be associated with the traits of interests, and used to predict the performance of these traits, and to select high performing lines in lieu of direct phenotyping. Molecular fingerprints can be generated based on whole genome sequences, which is costly and time consuming, and often times not practical. The genome complexity could be reduced using various methods before sequencing to produce fingerprints that are based on a small representation (selected regions or loci) of the genome. The present invention provides a more efficient and cost effective approach than the current art, which involves PCR-based detection of a plurality of genetic polymorphisms. Herein, selected polymorphic regions/loci are PCR amplified and then directly genotyped using HT sequencing. Multiplex PCR can be used to amplify as many as hundreds of thousands of such regions/loci simultaneously. Multiplexing samples by using DNA tags can further take advantage of the massive sequence information generated per run by HT sequencing methodologies.

For molecular fingerprinting, the first step is to select the polymorphic regions or loci to be used to generate the nucleotide sequence-based molecular fingerprints. SNPs are one source of candidate loci although they are not the only source. The number of loci used is determined by many factors including, but not limited to, the objectives and budgets of the projects as well as the structure of the genomes under investigation.

For example, we select 384 corn SNPs to demonstrate the molecular fingerprinting process although the capacity of a single HT sequencing run allows for the use of a much larger set of SNPs. A single channel of the Illumina Genome Analyzer flow cell can generate around 6 million sequence reads per sequencing run. Therefore approximately 300,000 loci can be genotyped simultaneously with about 20× sequence redundancy. If a smaller number of loci are needed, ~3,000 loci from 96 different samples can be sequenced at the same time by multiplexing samples (see below). These 384 SNPs are chosen from a larger pool of SNPs on the basis of features including even distribution in the corn genome and polymorphism information content (PIC) values of more than 3.0 in an attempt to maximize the information content. A portion of the SNPs are linked to important performance-related characteristics in corn.

The second step is to amplify the selected loci using multiplexing PCR. A pair of oligonucleotides is synthesized for each SNP, with one of them matching the nucleotide sequence that is 5' to the polymorphic nucleotide in the SNP and the other complementary to the region 3' of polymorphic nucleotide. For optimal sequencing results, although not necessary, the two oligonucleotides are separated by a length that matches the fragment size suggested by the HT sequencing methodologies (50 to 150 nucleotides for Illumina Genome Analyzer), with one of them adjacent to but not overlapping with the polymorphic nucleotide. To increase the efficiency of multiplexing PCR, the oligonucleotides for the 384 loci are designed so that they interfere with one another the least and that the resulting 384 PCR products have similar length and GC content. Two-stage PCR with bipartite oligonucleotides that containing a genome-specific sequence and a universal PCR primer can also help increase multiplexing PCR efficiency. When two-stage PCR is used, the employed HT sequencing methodology needs to be able to sequence through the universal PCR primer and the genome-specific oligonucleotides to reach the polymorphic nucleotide(s) of interest. Otherwise, the PCR products need to be processed to ensure that sequencing read into the polymorphic nucleotide(s). Another option would be to use the sequencing primer as part of universal PCR primer (see example 2) to cut down the number of nucleotides between the sequencing primer and the nucleotide(s) to be sequenced.

Although it is possible to pool loci "as you go" based on the objective of the experiment and/or the informativeness of individual locus in a given sample population, for molecular fingerprinting the selected loci are usually used as a fixed set. The 384 pairs of oligonucleotides (one for each chosen locus) are diluted in water and pooled together to a final concentration of 5 nM for each oligonucleotide.

DNA is prepared from each corn line to be fingerprinted using standard extraction protocols. About 100 ng of each DNA (varying depending on the number of loci used and the size of the genome) is dispensed into 96- or 384-well microtitre plates depending on the number of lines in an experiment and sample multiplexing format. In this example, we fingerprint 96 corn inbred lines. To each well, a PCR master mix is added along with high fidelity DNA polymerase according to standard PCR protocols. Finally, the mixture of the 384 pairs of oligonucleotides is added to each well to a final concentration of 0.5 nM per oligonucleotide and a final volume of 10 μL. An example PCR profile would be 94 C for 1 min, 55 C for 2 min, and ramping from 55 C to 72 C within 7 min for 25 cycles, followed by 72 C for 7 min. Any PCR protocol can be used as long as enough specific products from all the selected loci are generated for HT sequencing. To minimize PCR amplification errors and uneven amplification among loci, amplification is controlled by reducing the number of cycles and/or amount of oligonucleotides. The goal is to generate the amount of PCR products that are equivalent of the starting DNA suggested by the HT sequencing methodologies.

The PCR products are then purified according to the HT sequencing requirements before being ligated to sequencing adapters. The template genomic DNA used in PCR will not compete with the PCR products significantly in the downstream sequencing reactions due to the large size of genomic DNA. For optimal results, the template DNA can be removed from the PCR products using methods that are known in the art. In fact, if Qiagen purification columns are used to purify the PCR products for ligation, the majority of genomic DNA will be removed. In this example, Qiagen PCR purification kits (96 well format, according to manufacturer's instructions) are used to purify the PCR products and to remove the template genomic DNA (genomic DNA binds to the columns very tight due to its size and is difficult to elute).

Finally, the PCR products are ligated to the sequencing adapters for Illumina Genome Analyzer HT sequencing. Other methodologies are known in the art and are within the spirit and scope of this invention. In fact, if universal primers are used in a two-stage PCR scheme and the adapter sequences are used as universal primers, ligation of PCR products to adapters is not necessary since they are introduced through PCR already.

To take advantage of the massive sequence information generated by the Illumina Genome Analyzer sequencing technology, multiple samples are pooled in sequencing reactions and then deconvoluted using DNA tag sequences. DNA tags are usually 2-6 nucleotides (16 to 4096 unique tags for multiplexing) although longer sequences are desired so that samples are distinguished by more than one nucleotide difference to reduce error. The level of sample multiplexing is determined by the number of sequencing reads generated per run, the number of loci used and the desired level of redundancy, among other factors. The DNA tags can be introduced into the sequencing templates (PCR products in this case) using various methods including the one in example 2, i.e. including the DNA tag sequences in PCR primers. Or different versions of the adapters can be synthesized, with each version having one of the unique DNA tag sequences added at the 3' end; then each version is used for one of the samples in a multiplexing set. In this example, we use the set of 96 adapters provided by Illumina Genome Analyzer, and each adapter, according to the manufacturer's instructions, is ligated to the PCR product in one of the 96 wells in the PCR plate that corresponds to one of the 96 samples in a sample multiplexing format. The ligated products in the 96 wells are then combined into a single well, and used for HT sequencing reaction according to Illumina Genome Analyzer's sequencing protocols. The same oligonucleotide mixture of 384 SNPs can be used to amplify more samples, and PCR products from each plate of 96 samples can be ligated to the 96 versions of the adapters and pooled into one well for HT sequencing. Each Illumina Genome Analyzer flow cell can process up to 8 such pools per sequencing run.

The sequences obtained from the HT sequencing reactions are first binned according to the DNA tag sequences, assigning sequences to the 96 samples in a pool. Within each bin, the sequences are further grouped based on the sequences of the oligonucleotides that are adjacent to the polymorphic nucleotide(s) and used to amplify the PCR products. There should be 384 groups of sequences in each bin, with each one corresponding to each of the 384 SNP loci. The sequences are then analyzed to determine which allele is present at each of the 384 loci in each of the 96 samples.

The sequence information is used to determine the presence or absence of a particular nucleotide sequence or a particular variant of the nucleotide sequence at a locus that can be used to correlate with the performance of economically important traits. Once the association is established, with a particular sequence or sequence variant being the cause of or being tightly linked to the trait(s) of interest, the sequence can be used to predict the performance of these trait(s) and to select high performing parents, testers or progenies in lieu of direct phenotyping. The sequences or sequence variants can also be used to estimate, and for the purpose of increasing, the frequency of favorable sequences or sequence variants.

Sometimes, combinations of several nucleotide sequences or variants of nucleotide sequences at multiple loci are more predictive of certain traits. Using the sequence or variant combinations at closely linked loci, that is, defining haplotypes within pre-determined haplotype windows, is more informative and predictive than treating the loci individually. The other advantage of using combinations of sequences at linked loci is that only a subset of loci is needed to have information about the whole genome because chromosomes are inherited in linkage disequilibrium blocks (haplotype windows) and sequence information at selected loci (tagging loci) from one block can give information for all the loci on the block.

Example 4. Molecular Fingerprinting Soybeans Using HT Sequencing (Sequence Directed Fingerprinting)

The present invention provides a more efficient and cost effective approach than the current art, which involves PCR-based detection of a plurality of genetic polymorphisms. Herein, selected soybean polymorphic regions/loci were amplified and then directly genotyped using HT sequencing. In the present example 1536 loci were evaluated using Illumina Genome Analyzer HT sequencing technology. The present example also provides methods for indirect sequencing, wherein allele-specific tags were incorporated into corresponding template so that only the tag needs to be sequenced to infer the polymorphism.

As depicted in FIGS. 2-5, there are multiple strategies for genome complexity reduction. For the purpose of fingerprinting, one may wish to employ one or more of the complexity reduction methods known in the art. In the present example, existing PCR-based SNP assays were leveraged to target known polymorphisms using PCR primers corresponding to the SNPs as shown in FIG. 4 (direct fingerprinting) or allele-specific extension/ligation as illustrated in FIG. 5 (indirect fingerprinting). Leveraging an existing SNP library is particularly advantageous for referencing one or more databases with historic genotype information with a core set of SNPs.

Next, incorporation of DNA tags is used in order to enable sample multiplexing. In the present example, each sample in a multiplex set was assigned a unique DNA tag, i.e., a sequence tag differing by at least one base pair from the other barcodes in the set. In a preferred aspect, the percentage of G and C bases is balanced to minimize bias in the sequencing process. The DNA tag can range in length from about 2 to about 20 bp. In the present example, with 96 samples (germplasm samples), 5 bp sequences were used for the DNA tags with each DNA tag differing by 2 or more nucleotides (Table 2). These sample DNA tags were incorporated into the allele-specific tags and these allele-specific oligonucleotides were added to the allele-specific extension/ligation projects using PCR. In other aspects the allele-specific tags could be added to the extension/ligation products using a ligation reaction.

TABLE 2

Exemplary 5 nucleotide DNA tags for 96 samples.

| Well | Code |
| --- | --- |
| A1 | AAGCT |
| B1 | ACACA |
| C1 | ACAGC |
| D1 | ACCAG |
| E1 | ACCTA |
| F1 | ACGAA |
| G1 | ACGGT |
| H1 | ACGTC |
| A2 | ACTAC |
| B2 | ACTCT |
| C2 | AGACT |
| D2 | AGCAC |
| E2 | AGCGA |
| F2 | AGGAT |
| G2 | AGGCA |
| H2 | AGGTG |
| A3 | AGTAG |
| B3 | AGTTC |
| C3 | ATCCA |
| D3 | ATCTC |
| E3 | ATGAG |
| F3 | ATGCC |
| G3 | ATGGA |
| H3 | CAACT |
| A4 | CAAGA |
| B4 | CACAG |
| C4 | CACGT |
| D4 | CACTC |
| E4 | CAGAC |
| F4 | CAGCA |
| G4 | CAGTG |
| H4 | CATCC |

TABLE 2-continued

Exemplary 5 nucleotide DNA tags for 96 samples.

| Well | Code |
|------|------|
| A5 | CCAAG |
| B5 | CCCAA |
| C5 | CCTAT |
| D5 | CCTGA |
| E5 | CCTTC |
| F5 | CGATC |
| G5 | CGCAT |
| H5 | CGGTA |
| A6 | CGTAC |
| B6 | CGTGT |
| C6 | CGTTG |
| D6 | CTACC |
| E6 | CTCAC |
| F6 | CTCGA |
| G6 | CTCTG |
| H6 | CTGAT |
| A7 | CTGTC |
| B7 | CTTAG |
| C7 | CTTCT |
| D7 | GAACA |
| E7 | GAATC |
| F7 | GACAT |
| G7 | GACGA |
| H7 | GAGAG |
| A8 | GATAC |
| B8 | GATGT |
| C8 | GATTG |
| D8 | GCAAC |
| E8 | GCACT |
| F8 | GCAGA |
| G8 | GCATG |
| H8 | GCGTA |
| A9 | GGTCT |
| B9 | GGTGA |
| C9 | GTACG |
| D9 | GTAGC |
| E9 | GTCCT |
| F9 | GTCTA |
| G9 | GTGGT |
| H9 | GTGTG |
| A10 | GTTCA |
| B10 | GTTTC |
| C10 | TACCT |
| D10 | TACGC |
| E10 | TACTG |
| F10 | TAGGT |
| G10 | TAGTC |
| H10 | TATCG |
| A11 | TCATC |
| B11 | TCCAC |
| C11 | TCCCA |
| D11 | TCGAT |
| E11 | TCGGA |
| F11 | TCGTG |
| G11 | TCTAG |
| H11 | TCTCC |
| A12 | TCTGT |
| B12 | TGACC |
| C12 | TGAGA |
| D12 | TGATG |
| E12 | TGCAA |
| F12 | TGCTC |
| G12 | TGGAG |
| H12 | TGTCA |

This fingerprinting example included 1536 soybean SNPs, wherein each SNP was treated as bi-allelic and thus had two allele-specific oligonucleotides (allele-specific tag plus sample DNA tag) and one locus-specific oligonucleotide (FIG. 7). The locus-specific oligonucleotide comprised a universal adapter sequence at the 3' end, though the universal adapter sequence could also be part of the primer needed for downstream sequencing (i.e., the Illumina PCR 2.1 primer). The allele-specific oligonucleotides were about 15 nucleotides in length, with balanced melting temperatures.

To prepare template for sequencing, DNA was prepared for each of the tissue samples as described above. To generate the allele-specific extension/ligation products, the allele-specific tags and locus-specific oligonucleotides were mixed with template, with an initial heating at 70° C., then cool down gradually, followed by 15 minutes at 45° C. for DNA polymerase and ligase reactions, as depicted in FIG. 5.

Figure 12:
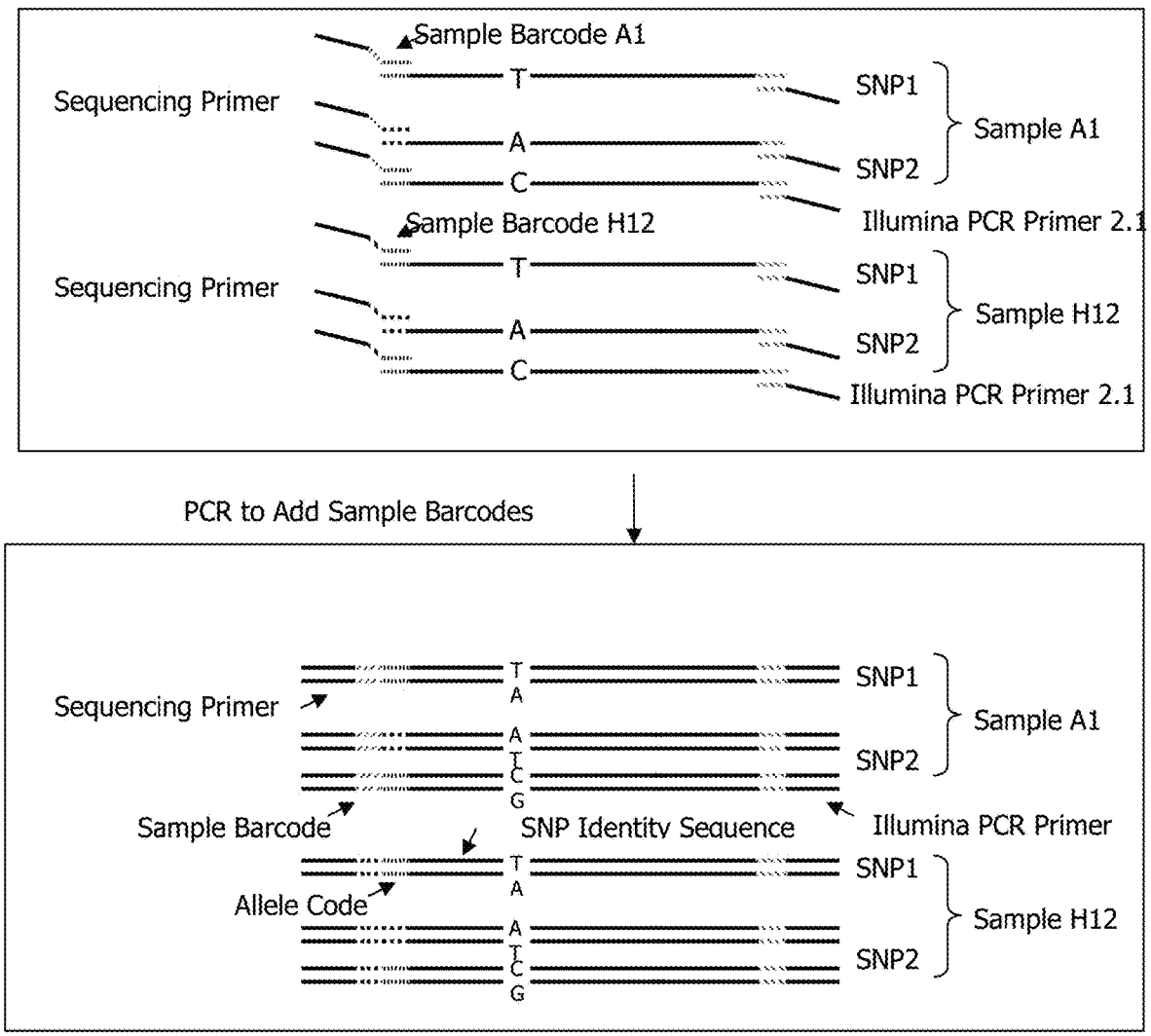
FIG. 12 illustrates a strategy for adding sample DNA tags with allele-specific extension/ligation as described in Example 4.

After extension/ligation, products were purified using magnetic beads as known in the art. A subsequent PCR was conducted to add the sample DNA tag, which was added next to the allele-specific tag as illustrated in FIG. 12. 96 (×2) forward primers were used, corresponding to 96 germplasm samples. In addition, the Illumina Genome Analyzer genomic sequencing primer was added to the 5' end, wherein the 5' end, plus 5-nt sample barcodes (96 versions) plus 15/16-nt allele codes (2 versions). A single reverse primer was used, which corresponds to the universal adapter sequence, and the Illumina Genome Analyzer PCR primer 2.1 was added to the 5' end of this reverse primer. PCR master mix was added to 5 µL of extension/ligation products, along with 0.3 U high fidelity DNA polymerase according to standard PCR protocol, with a final reaction concentration of 0.16 µM primers, 0.1 mM dNTPs in a final volume of 25 µL. The plate was heated to 95° C. for nine minutes to denature the DNA. Fifteen cycles of PCR were then completed using the following conditions: 94° C. for 30 sec, 50° C. for 30 sec, 72° C. for 2 min, followed by a final 10 minute extension at 72° C.

Approximately 5-10 ng of the purified template was amplified with enrich PCR per Illumina Genome Analyzer specifications. The enrich PCR also adds the adapter required for the downstream bridge PCR reaction if the adapters were not already incorporated in the primers. The enrich PCR product is purified, again using PCR purification methods known in the art, and the resulting template is sequencing per Illumina Genome Analyzer specifications.

Figure 13:
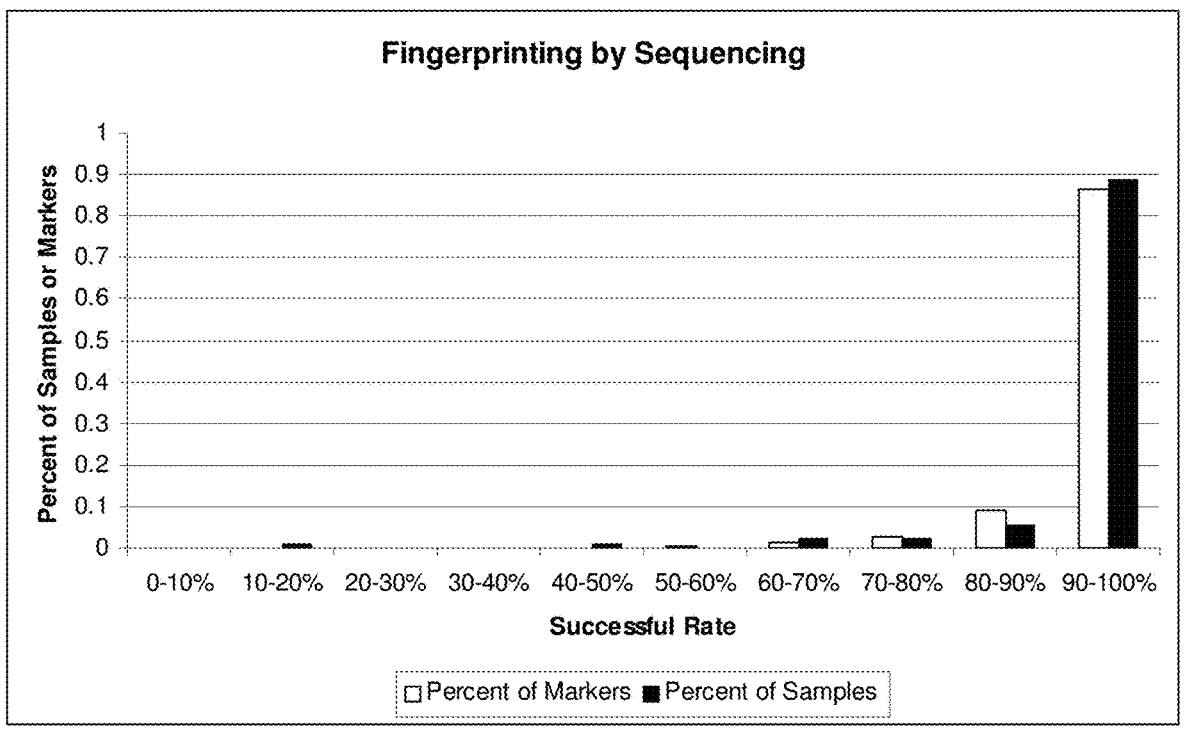
FIG. 13 illustrates the success rate of fingerprinting using high throughput sequencing technology for 1536 SNPs in 96 soybean varieties as described in Example 4.

The sequences obtained from the sequencing reaction were binned according to the DNA tag sequence and allele-specific tag sequence. FIG. 13 shows the success rate for the markers and the soybean samples, with nearly 90% of the markers and the germplasm entries having a call rate between 90 and 100%. The present example used allele-specific tags which offers an advantage in sequence deconvolution such that the genotype of a sample could be assigned based on the first 20 base pairs since the first 5 base pairs identified the germplasm sample and the next 15 base pairs represented the allele. In other embodiments, the DNA tag could be as short as 2 base pairs and the allele-specific tag could be as short as two base pairs to further reduce the sequence read needed to genotype. In a preferred embodiment, the methods of the present invention anticipate inferring genotype based on just a 2 base pair tag, depending on the degree of multiplexing. In still another aspect, the methods of the present invention anticipate inferring genotype based on a single base pair.

The ability to simultaneously generate large amounts of fingerprint data, coupled with the flexibility to either saturate specific regions with contiguous sequence or leverage known polymorphic sites for fingerprint data across a haplotype, chromosome, or even genome provides a valuable tool for germplasm improvement activities, experimental work to identify genomic regions of interest, quality assurance and control, and monitoring IP protection.

Example 5. Complexity Reduction Sequencing Using DNA-Tagged Random Primers

One aspect of this invention is the ability to simultaneously sequence multiple nucleic acid templates which may comprise samples from different individuals or pooled individuals as well as multiple loci.

In this example, we utilize random primers (hexamer to decamers depending on the project) labeled with a coding system. The coding system will consist of a series of non-native nucleotide sequences ranging from two nucleotides to half the length of the random primer. Mixtures of random primers labeled with at least two DNA tags will be created to amplify and identify any number of genomes or portions of genomes. The amplified sequences are then determined by any number of sequencing methods including, but not limited to, Sanger sequencing using the ABI 3730 or similar platform, pyrosequencing using a 454 or similar platform, and sequencing by synthesis using a Illumina Genome Analyzer sequencing instrument or similar platform. It is anticipated that this method will be used on new sequencing technologies as they arise.

This aspect of the present invention will allow researchers to pool DNA samples saving valuable monetary and time resources on sequencing. To evaluate multiple genomes or genomic regions simultaneously, each template will be amplified independently with a different set of DNA-tagged random primers. The length of the random primer is be dictated by level of complexity of the genome; the more repeat sequences, the longer the primer will need to be in order to selectively exclude these regions. Once the genomes are amplified they can be purified by standard methods specific to a given sequencing technology. To make later steps easier, the random primers could also be labeled with a capture molecule such as biotin.

After amplification, the purified DNA can be sequenced by any number of nucleic acid sequencing methods and compared to identify genome diversity and which specific genomes contribute to the diversity. The present invention could be used without the DNA tags but then once pooled for sequencing there is no way to "de-pool" the sequences and further evaluation either through sequencing or specific genotyping reactions are required.

This method provides a highly novel method of applying sequence tags to multiplex genome sequencing and genotyping.

Example 6. Mining Rare Alleles

The use of direct nucleic acid sequence data enables detection of rare alleles or haplotypes in the genome of a plant. This is particularly important for leveraging rare but important genomic regions in a breeding program, such as a disease resistance locus from exotic or unadapted germplasm, wherein rare alleles are defined as occurring in low frequency within the germplasm pool and potentially being previously undetected within the germplasm pool. The present example provides methods for rare allele detection, experimental design (i.e., selecting exotic germplasm, germplasm with known phenotype of interest, screening non-elite gp), and utility (i.e., introgression programs for beneficial rare variants for specific traits and/or to expand germplasm diversity in one or more specific germplasm pools such as per maturity zone).

A set of germplasm comprising at least 2 germplasm entries is provided. Non-limiting factors influencing inclusion in a sequencing project for at least one locus include germplasm origin or geography, at least one genotype of interest, at least one phenotype of interest, performance in hybrid crosses, performance of a transgene, and other observations of the germplasm or predictions relating the germplasm and its performance.

Using the methods and approaches presented herein, at least one base pair is sequenced for at least 2 germplasm entries. Using methods known in the art for sequence alignment and in silico evaluation, differences and similarities are identified and linked to the source germplasm entry. Following identification of alleles of interest, selection decisions can be made.

In the case of rare allele mining, the rare allele may be associated with a known phenotype. In addition, the identification of the rare allele can provide the basis for additional phenotyping, association studies, and other assays to evaluate the effect of the rare allele on plant phenotype and breeding performance. Further, the direct nucleic acid sequence of the rare allele can be immediately leveraged for use as a marker via methods known in the art and described herein to detect this rare allele in additional germplasm entries, to be used as a basis for selection, and to facilitate introgression of the rare allele in germplasm entries lacking the rare allele. In other aspects, the rare allele is isolated and the isolated nucleic acid is transformed into a plant using methods known in the art in order to confer a preferred phenotype to the recipient plant. The recipient plant can subsequently be used as a donor for conversion programs to cross with elite germplasm for trait integration purposes.

The identification of rare alleles is useful for leveraging the full genetic potential of any germplasm pool, i.e., set of 2 or more germplasm entries. This is useful for determining breeding cross strategy, increasing the diversity between 2 or more germplasm pools, evaluating heterotic pools, and informing breeding decisions. High throughput sequencing both accelerates the identification of the alleles and allows simultaneous detection of rare alleles and identification of associated markers.

---

We claim:

1. A method of identifying a phenotypic trait of interest in a plant, the method comprising:
   providing at least two plant DNA samples, wherein at least one of the plant DNA samples comprises a polymorphism associated with a phenotypic trait of interest;
   amplifying at least two different loci in each genome of each plant DNA sample in a single multiplex PCR reaction, wherein each of said loci is amplified with at least one specific primer and tagged with at least one DNA tag;
   combining at least two of the amplified DNA samples to create a pool of amplified DNA samples;
   sequencing the pool of amplified DNA samples;
   comparing the sequence information from the amplified DNA samples to a consensus sequence to identify the presence or absence of the polymorphism, wherein the individual DNA samples are identified by the DNA tags; and
   selecting one or more plants based on the presence or absence of the polymorphism in the plant DNA sample.

2. The method as set forth in claim 1, wherein the plant is selected from the group consisting of a forage crop, oilseed crop, grain crop, fruit crop, ornamental plants, vegetable crop, fiber crop, spice crop, nut crop, turf crop, sugar crop, beverage crop, tuber crop, root crop, and forest crop.

3. The method as set forth in claim 1, wherein the polymorphism is indicative of an economically important trait in a plant and wherein said economically important trait is selected from the group consisting of herbicide tolerance, disease resistance, insect or pest resistance, altered fatty acid, protein or carbohydrate metabolism, increased grain yield, increased oil, enhanced nutritional content, increased growth rates, enhanced stress tolerance, preferred maturity, enhanced organoleptic properties, altered morphological characteristics, and sterility.

4. The method of claim 1, wherein the polymorphism is selected from the group consisting of a single nucleotide polymorphisms (SNPs), insertions or deletions in DNA sequence (Indels), simple sequence repeats of DNA sequence (SSRs), a restriction fragment length polymorphism, and a variation in copy number.

5. The method of claim 1, wherein the polymorphism is a transgene.

6. A method of identifying a phenotypic trait of interest in a plant, the method comprising:
   providing at least two plant DNA samples, wherein at least one of the plant DNA samples comprises a polymorphism associated with a phenotypic trait of interest;
   amplifying at least two different loci in each genome of each plant DNA sample in a single multiplex PCR reaction, wherein each of said loci is amplified with at least one specific primer comprising at least one DNA tag and at least one allele-specific tag;
   combining at least two of the amplified DNA samples to create a pool of amplified DNA samples;
   sequencing the allele-specific tags in the pool of amplified DNA samples;
   comparing the sequence information from the allele-specific tags to a known library of allele-specific tags to identify the presence or absence of the polymorphism in individual DNA samples, wherein the individual DNA samples are identified by the DNA tags; and
   selecting one or more plants based on the presence or absence of the polymorphism in the plant DNA samples.

7. The method of claim 6, wherein the polymorphism is selected from the group consisting of single nucleotide polymorphisms (SNPs), insertions or deletions in DNA sequence (Indels), simple sequence repeats of DNA sequence (SSRs), a restriction fragment length polymorphism, and a variation in copy number.

8. The method of claim 6, wherein the polymorphism is a transgene.

9. The method of claim 6, wherein the plant is selected from the group consisting of a forage crop, oilseed crop, grain crop, fruit crop, ornamental plants, vegetable crop, fiber crop, spice crop, nut crop, turf crop, sugar crop, beverage crop, tuber crop, root crop, and forest crop.

10. The method as set forth in claim 6, wherein the polymorphism is indicative of an economically important trait in a plant and wherein said economically important trait is selected from the group consisting of herbicide tolerance, disease resistance, insect or pest resistance, altered fatty acid, protein or carbohydrate metabolism, increased grain yield, increased oil, enhanced nutritional content, increased growth rates, enhanced stress tolerance, preferred maturity, enhanced organoleptic properties, altered morphological characteristics, and sterility.

* * * * *